United States Patent
Loskill et al.

(10) Patent No.: US 11,591,555 B2
(45) Date of Patent: Feb. 28, 2023

(54) METHOD FOR CULTIVATING CELLS

(71) Applicant: NMI Naturwissenschaftliches und Medizinisches Institut an der Universität Tübingen, Reutlingen (DE)

(72) Inventors: Peter Loskill, Stuttgart (DE); Oliver Schneider, Kempten (DE)

(73) Assignee: FRAUNHOFER-GESELLSCHAFT ZUR FÖRDERUNG DER ANGEWANDTEN FORSCHUNG E.V., Reutlingen (DE)

( * ) Notice: Subject to any disclaimer, the term of this patent is extended or adjusted under 35 U.S.C. 154(b) by 516 days.

(21) Appl. No.: 16/621,046

(22) PCT Filed: Jun. 13, 2018

(86) PCT No.: PCT/EP2018/065723
§ 371 (c)(1),
(2) Date: Dec. 10, 2019

(87) PCT Pub. No.: WO2018/229160
PCT Pub. Date: Dec. 20, 2018

(65) Prior Publication Data
US 2020/0109361 A1    Apr. 9, 2020

(30) Foreign Application Priority Data
Jun. 13, 2017 (DE) .................... 10 2017 209 942.9

(51) Int. Cl.
C12M 1/10        (2006.01)
C12M 3/00        (2006.01)
(Continued)

(52) U.S. Cl.
CPC ........... *C12M 23/12* (2013.01); *B01L 3/5027* (2013.01); *C12M 23/16* (2013.01); *C12M 27/10* (2013.01);
(Continued)

(58) Field of Classification Search
CPC ...... C12M 23/12; C12M 23/16; C12M 27/10; C12M 29/00; C12M 29/12; B01L 3/5027; B01L 2300/0803
(Continued)

(56) References Cited

U.S. PATENT DOCUMENTS

2005/0106714 A1    5/2005   Zarur et al.
2010/0323434 A1   12/2010   Yang

FOREIGN PATENT DOCUMENTS

GB     2 350 678 A    12/2000
WO     99/55827 A     11/1999
(Continued)

OTHER PUBLICATIONS

International Search Report dated Oct. 5, 2018 for corresponding International Application No. PCT/EP2018/065723.
(Continued)

*Primary Examiner* — Fred Prince
(74) *Attorney, Agent, or Firm* — Pearne & Gordon LLP

(57) ABSTRACT

The present invention relates to a method for cultivating cells, in particular tissues, comprising a carrier plate unit, which has at least one access opening, at least one cultivation chamber, and at least one channel connecting the access opening to the cultivation chamber.

24 Claims, 31 Drawing Sheets

(51) Int. Cl.
*C12M 1/32* (2006.01)
*C12M 3/04* (2006.01)
*C12M 1/00* (2006.01)
*B01L 3/00* (2006.01)
*C12M 3/06* (2006.01)

(52) U.S. Cl.
CPC ............ *C12M 29/00* (2013.01); *C12M 29/12* (2013.01); *B01L 2300/0803* (2013.01)

(58) Field of Classification Search
USPC .................... 435/325, 347, 366, 394, 400
See application file for complete search history.

(56) References Cited

FOREIGN PATENT DOCUMENTS

| WO | 02/102969 A2 | 12/2002 |
| WO | 2013/086486 A1 | 6/2013 |
| WO | 2013/086502 A1 | 6/2013 |
| WO | 2015/013210 A1 | 1/2015 |
| WO | WO 2017/027384 A1 * | 2/2017 |

OTHER PUBLICATIONS

Written Opinion dated Oct. 5, 2018 for corresponding International Application No. PCT/EP2018/065723.

Jin-Young Kim et al.; "3D Spherical Microtissues and Microfluidic Technology for Multi-Tissue Experiments and Analysis"; Journal of Biotechnology; 205; 2015; pp. 4-35 (cited in the specification).

Joshi; "Cells and organs on a chip-a revolutionary platform for biomedicine"; Lab-on-a-Chip Fabrication and Application, M. Stoytcheva (Ed.), InTech (2016), pp. 92-108.

International Preliminary Report on Patentability dated Dec. 17, 2019 for corresponding International Application No. PCT/EP2018/065723.

* cited by examiner

METHOD FOR CULTIVATING CELLS

FIELD OF THE INVENTION

The present invention relates to a method for producing a cell complex, comprising providing cells and a device for cultivating cells, in particular tissues, comprising a carrier plate unit, which has at least one access opening, at least one cultivation chamber, and at least one channel connecting the access opening to the cultivation chamber, and cell complexes produced by means of the method.

BACKGROUND OF THE INVENTION

Microfluidic organ-on-a-chip systems, also called tissue chips, or micro-physiological systems (MPS), in which cells and tissue are cultivated in ultrasmall scale and pharmaceutical or cosmetic substances can be tested, have developed in recent years from a conceptual idea to a disruptive new technology. A high potential as an animal experiment alternative and screening tool in pharmaceutical development, toxicity determination, and personalized medicine is ascribed thereto. The basic principle of organ-on-a-chip systems is the provision of a controlled, micrometer-dimensioned environment for cultivating human and animal organ tissue and cells.

Cells, cell clusters, or tissue components have to be introduced into the micrometer-dimensioned environments for the integration and/or generation of tissue in the organ-on-a-chip systems. To be able to generate physiological cell densities in accordance with the in vivo tissue, especially in the case of non-proliferating cell types, the cells, cell clusters, or tissue components already have to be injected initially in high density. This is often only possible by way of complicated methods having high variability and significant strain of the injected cells.

In most cases, in particular in the case of proliferating cells, the cells are injected in variable density and the desired cell density is thereupon achieved by differentiation and/or proliferation of the cells in the chip. To transport the cells in the culture chambers and/or to achieve initially high cell densities therein, pressure gradients are generated in the prior art, so that cell suspensions are injected with positive pressure into the micro-channels or are suctioned with negative pressure into the channels (PCT/US2014/047482; A. Mathur, P. Loskill, K. Shao, N. Huebsch, S. Hong, S. G. Marcus, N. Marks, M. Mandegar, B. R. Conklin, L. P. Lee, et al., *Sei. Rep.* 2015, 5, 8883). Alternatively, individual cells can also be applied with the aid of bioprinting directly onto the chip (S. Knowlton, B. Yenilmez, S. Tasoglu, *Trends Biotechnol.* 2016, 34, 685-688) or preformed spheroids are injected (N. S. Bhise, J. Ribas, V. Manoharan, Y. S. Zhang, A. Polini, S. Massa, M. R. Dokmeci, A. Khademhosseini, *J. Control. Release* 2014, 190, 82-93; J.-Y. Kim, D. A. Fluri, R. Marchan, K. Boonen, S. Mohanty, P. Singh, S. Hammad, B. Landuyt, J. G. Hengstier, J. M. Keim, et al., *J. Biotechnol.* 2015, 205, 24-35).

The methods and devices known in the prior art for cultivating cells, in particular for cultivating and providing high cell densities, in particular for producing cell complexes and tissues, are frequently disadvantageous with respect to the cell culture conditions used, which negatively affect the survivability and/or ability to culture the cells, for example, elevated shear forces and/or pressure gradients.

BRIEF SUMMARY OF THE INVENTION

The fundamental technical problem of the present invention is therefore to provide an improved method for producing cell complexes, which overcomes the above-mentioned disadvantages in the prior art, in particular enables cells to be cultivated and cell complexes to be produced without subjecting them to a disadvantageous strain, for example, undefined pressure or shear forces.

In particular, the fundamental technical problem is to provide a method which is capable of cultivating cells in particularly high, preferably physiological cell density and of producing cell complexes, in particular tissue, microscopic tissue, organs, or organ equivalents.

The present invention solves its fundamental technical problem by providing a method for producing a cell complex comprising a) providing cells and a device for cultivating cells, comprising a carrier plate unit having at least one access opening, at least one cultivation chamber, and at least one channel connecting the at least one access opening to the at least one cultivation chamber, b) introducing the cells into the device through the at least one access opening, c) introducing the device into a rotational device enabling a rotation of the device, d) setting the device into rotation, e) receiving cells in the at least one cultivation chamber, and f) cultivating the cells in the at least one cultivation chamber, wherein a cell complex, in particular a three-dimensional cell complex, results due to the cultivation of the cells in the at least one cultivation chamber.

The present invention therefore provides a method for producing a cell complex, wherein this method uses devices for cultivating cells which are preferably microfluidic devices. These microfluidic devices have a carrier plate unit having at least one access opening, at least one cultivation chamber, and at least one channel connecting the at least one access opening to the at least one cultivation chamber.

The present invention accordingly provides providing cells and such a device, introducing the cells into the device through the at least one access opening, then introducing the device into a device enabling the rotation of the device, setting the rotational device into rotation, wherein cells are received in the at least one cultivation chamber and cultivated therein due to the setting into rotation of the device, and wherein a cell complex, in particular a three-dimensional cell complex, results due to the cultivation of the cells in the at least one cultivation chamber.

In one particularly preferred first embodiment of the present invention, the device for cultivating cells has a carrier plate unit having a central axis of rotation, wherein in this design the at least one access opening is arranged proximally to this central axis of rotation and the at least one cultivation chamber is arranged distally to this central axis of location.

In particular, the present invention therefore solves its fundamental technical problem by providing a method for producing a cell complex, comprising a1) providing cells and a device for cultivating cells, in particular a, preferably three-dimensional, cell culture system, comprising a carrier plate unit, which has a central axis of rotation, having at least one access opening arranged proximally to the axis of rotation, at least one cultivation chamber arranged distally to the axis of rotation, and at least one channel connecting the at least one access opening to the at least one cultivation chamber, b1) introducing the cells into the device through the at least one access opening, c1) introducing the device into a rotational device enabling a rotation of the device, d1) setting the device into rotation, e1) receiving cells in the at least one cultivation chamber, and f1) cultivating the cells in the at least one cultivation chamber, wherein a cell complex, in particular a three-dimensional cell complex, results due to the cultivation of the cells in the at least one cultivation chamber.

In one particularly preferred embodiment, the device for cultivating cells is a carrier plate unit, in particular a carrier plate, having the at least one access opening arranged thereon, at least one cultivation chamber, and at least one channel connecting the at least one access opening to the at least one cultivation chamber.

In one particularly preferred embodiment, the device for cultivating cells is a carrier plate unit, in particular a carrier plate, which has an axis of rotation, having at least one access opening arranged proximately to the axis of rotation, at least one cultivation chamber arranged distally to the axis of rotation, and at least one channel connecting the at least one access opening to the at least one cultivation chamber. In particular, the device preferably used according to the invention is designed so that it can be rotated, i.e., can be set into rotation, around its central axis of rotation.

The concept of central axis of rotation is understood in conjunction with the present invention as the straight line around which the device can rotate and which in particular corresponds to the axis of symmetry of the macroscopic shape of the device having the maximum main moment of inertia and which extends through the geometrical center point of the device. In particular, the central axis of rotation stands vertically on the preferably circular device seen in a top view.

The device provided according to the invention for cultivating cells therefore comprises in one preferred embodiment a carrier plate unit having a central axis of rotation, in particular consists thereof, wherein the carrier plate unit has at least one access opening, which is accessible from outside the carrier plate unit, arranged proximately to the axis of rotation, at least one cultivation chamber arranged distally to the axis of rotation, and at least one channel, which is preferably radially aligned, connecting the access opening to the cultivation chamber. The at least one access opening, the at least one cultivation chamber, and the at least one channel connecting these two structures are formed in the body of the carrier plate unit, in particular the carrier plate, or on its surface. In one preferred embodiment, it is provided that the at least one access opening is arranged spatially in the vicinity, i.e., proximally, to the axis of rotation, while the at least one cultivation chamber is arranged distally, i.e., farther away from the axis of rotation, i.e., is provided in a peripheral region of the carrier plate unit. The distance ($r_1$) of the at least one access opening to the axis of rotation is therefore less than the distance ($r_2$) of the at least one cultivation chamber to the axis of rotation. The spatial arrangement provided according to the invention of the at least one access opening in relation to the at least one cultivation chamber has the result upon rotation of the device around its axis of rotation that because of the centrifugal force, the cells, cell culture medium, or cell suspension introduced into the access opening are conveyed in the direction of the centrifugal force into the peripheral regions of the carrier plate unit. In addition, interfering air bubbles are removed from the device in the opposite direction, i.e., in the direction of the access opening. In particular, the cells introduced into the access opening move with the aid of the centrifugal force via the at least one channel connecting the at least one access opening to the at least one cultivation chamber into the at least one cultivation chamber. If, as is provided in a preferred embodiment according to the invention, more than one access opening and more than one cultivation chamber are provided, it preferably applies to each individual one of the access openings and cultivation chambers that the cultivation chambers are arranged at a greater distance from the axis of rotation than the access openings, i.e., the cultivation chambers are arranged distally to the axis of rotation and the access openings are arranged proximally thereto. In particular, the at least one access opening is located at the distance $r_1$ from the central axis of rotation and the at least one cultivation chamber is located at the distance $r_2$ from the central axis of rotation, wherein $r_1 < r_2$.

The cells introduced through the access opening into the carrier plate unit, in particular the cell suspension, possibly also cell culture medium, are thus advantageously transported during a rotation of the device according to the invention, i.e., by the centrifugal force ($F_2 = m \omega^2 r$), from the at least one access opening arranged proximally to the axis of rotation through the at least one channel connecting the access opening to the cultivation chamber into the at least one cultivation chamber arranged distally to the axis of rotation. The rotation at angular velocity $\omega$ causes, at the distance $r_2$ of the at least one cultivation chamber, an acceleration of the cells or cell suspensions of $a = \omega^2 r_2$. The cells thus advantageously accumulate in the at least one cultivation chamber, i.e., in the peripheral region of the carrier plate unit. The cells are advantageously accumulated by centrifugal force in the at least one cultivation chamber without undefined pressures or shear forces acting on the cells. The cells can then be cultivated in the cultivation chamber, preferably with supply by culture medium, either with lesser rotation or without a further rotation of the device. The cultivation of the cells preferably has the result that the cells completely fill up the at least one cultivation chamber and thus form a three-dimensional cell complex. The device according to the invention advantageously enables tissue and cell complexes having high density to be produced in the at least one cultivation chamber in a manner which can be reproduced and parallelized, wherein the device is additionally easily operable.

In a further, second embodiment of the present invention, the fundamental technical problem of the invention is solved by providing a method for producing a cell complex, wherein the carrier plate unit of the device for cultivating cells does not have a central axis of rotation. In this embodiment, the carrier plate unit, after introducing the device into the rotational device enabling the rotation of the device and setting the device into rotation, does not rotate around a central axis of rotation, which is not provided, but rather around the axis of rotation of the rotational device. As in the carrier plate unit having the central axis of rotation, the at least one access opening, the at least one cultivation chamber, and the at least one channel connecting these two structures are formed in the body of the carrier plate unit, in particular the carrier plate, or in its surface. A suitable spatial arrangement provided according to the invention of the at least one access opening to the at least one cultivation chamber has the result, upon rotation of the device in a rotational device, that because of the centrifugal force, the cells, cell culture medium, or cell suspension introduced into the access opening are conveyed in the direction of the centrifugal force into the regions of the carrier plate unit in which the at least one cultivation chamber is provided. In addition, interfering air bubbles are removed from the device in the opposite direction, i.e., in the direction of the access opening. In particular, the cells introduced into the access opening move with the aid of the centrifugal force via the at least one channel connecting the at least one access opening to the at least one cultivation chamber into the at least one cultivation chamber. If, as is provided in one preferred embodiment according to the invention, more than one access opening and more than one cultivation chamber are provided, it thus preferably applies to each of the access openings and cultivation chambers that the cultivation chambers are arranged in such a way that after the introduction of the device into a rotational device enabling the rotation of the device and setting the device into rotation, the cells introduced into the access opening move through the channel into the at least one cultivation chamber because of the centrifugal force. The cells, in particular cell suspension, possibly also cell culture, introduced through the access opening into the carrier plate unit are thus advantageously transported during a rotation of the device according to the invention, i.e., by the centrifugal force ($F_z = m\,\Omega^2 r$) from the access opening through the at least one access opening having the channel connecting the cultivation chamber into the at least one cultivation chamber. The rotation at an angular velocity $\Omega$ causes an acceleration of the cells or suspensions. The cells thus advantageously accumulate in the at least one cultivation chamber. The cells are advantageously accumulated by centrifugal force in the at least one cultivation chamber, without defined pressures or shear forces acting on the cells. The cells can then be cultivated in the cultivation chamber, preferably with supply by culture medium, either with lesser rotation or without a further rotation of the device. The cultivation of the cells preferably has the result that the cells completely fill up the at least one cultivation chamber and thus form a three-dimensional cell complex. The device used according to the invention advantageously enables tissue and cell complexes having high cell density to be produced in the at least one cultivation chamber in a manner which can be reproduced and parallelized, wherein the device is additionally easily operable.

In this second embodiment of the present invention, the device used in the method for producing a cell complex for cultivating cells, in particular a carrier plate unit, has at least one access opening arranged proximally to the axis of rotation of the rotational device, at least one cultivation chamber arranged distally to the axis of rotation of the rotational device, and at least one channel connecting the access opening to the cultivation chamber.

The devices used according to the invention, i.e., the devices having a central axis of rotation and not having a central axis of rotation, are advantageous, inter alia, because they enable in particular a parallelization of cell culture devices, in particular organ-on-a-chip systems, by simultaneously introducing cells into a plurality of cultivation chambers. The devices and methods used according to the invention simplify the handling of micro-physiological in vitro cell culture systems, in particular also in that pumps are not used for the injection, i.e., the introduction of the cells, air bubbles can be eliminated from the device by the rotation, and also a short method duration and simpler handling capability are achieved and only one structural unit is used. It advantageously also results due to the rotation of the device that air enclosures in the cultivation chambers can be removed or avoided in a simple manner.

The devices and methods used according to the invention can in particular also be used as animal experimentation alternatives, for fundamental studies, but also in applied research and development, also as screening systems for therapeutic preparations or chemicals. In one particularly preferred embodiment, the devices used according to the invention and the methods according to the invention can be used for cultivating cells, in particular for producing cell complexes, for generating artificial tissue or mixed tissue, in particular also for regenerative and/or personalized medicine.

In one particularly preferred embodiment, the devices used according to the invention, in particular the carrier plate unit, comprises at least two carrier plates, in particular a first and a second carrier plate, but possibly three, four, five, six, or more carrier plates can also be provided.

In one preferred embodiment, the devices used according to the invention, in particular the carrier plate unit, in particular the first and second carrier plate, seen in a top view, has the shape of a circle. In particular, it is formed as an essentially planar, i.e., a flat three-dimensional body. In particular, the devices used according to the invention have the shape of a flat cylinder, in particular a disk. The horizontal planar extension of the devices used according to the invention, which are preferably provided according to the invention in flat, three-dimensional form, is therefore substantially greater than its vertical extension, wherein the horizontal extension of the device according to the invention, in particular the carrier plate, and the structures provided therein, such as openings, channels, and chambers, is referred to as the length and width and the vertical extension is referred to as the height. The area of the devices used according to the invention spanned by the length and width (length is the horizontal extension which is greater than the width), in particular of the first and second carrier plate, or of the structures thereof, is referred to as the horizontal area of the devices, carrier plate, or structures used according to the invention.

In one particularly preferred embodiment, the devices used according to the invention, in particular the carrier plate unit, seen in a top view, thus has a circular shape, wherein in one preferred embodiment the axis of rotation extends standing vertically on the circle through the center point of the device, which is provided as circular, in particular disk-shaped, viewed in a top view, and wherein the distance between the geometrical center point of the circle and the outer circumference of the circle is referred to as the radius r.

In one preferred embodiment of the invention, the diameter of the devices used according to the invention, which are preferably provided as disk-shaped, is 1 to 80 cm, in particular 5 to 64 cm, in particular 5 to 30 cm, preferably 7 to 20 cm, preferably 15 cm, particularly preferably 10 cm.

In a further preferred embodiment of the present invention, the devices used according to the invention, in particular the devices used according to the invention with or without central axis of rotation, in particular the carrier plate unit, in particular the first and second carrier plate, seen in a top view, has the form of a rectangle, preferably a square. However, other forms are also conceivable of the devices used according to the invention, in particular of the devices used according to the invention with or without central axis of rotation. In particular, the devices used according to the invention, in particular the carrier plate unit, in particular the first and second carrier plate, is formed as an essentially planar, i.e., flat three-dimensional body. In particular, the devices used according to the invention, in particular the devices used according to the invention with or without central axis of rotation have the form of a flat cuboid. The horizontal planar extension of the devices used according to the invention, which is preferably provided according to the invention in flat, three-dimensional form, is preferably substantially greater in this case than its vertical extension, wherein the horizontal extension of the devices used according to the invention, in particular the carrier plate, and also the structures provided therein, such as openings, channels, and chambers, is referred to as the length and width and the vertical extension is referred to as the height. The area of the devices used according to the invention spanned by the length and width (length is the horizontal extension, which is greater than the width), in particular of the first and second carrier plate, or of its structures, is referred to as the horizontal area of the devices, carrier plate, or structures used according to the invention.

In one particularly preferred embodiment of the present invention, the devices used according to the invention, in particular the carrier plate unit, in particular the first and second carrier plate, are designed as a micro-titration plate, in particular in the form of a micro-titration plate.

In a further preferred embodiment of the present invention, the devices used according to the invention, in particular the carrier plate unit, in particular the first and second carrier plate, are designed as a micro-titration plate, in particular in the form of a micro-titration plate, wherein the at least one access opening arranged proximally to the axis of rotation, in particular to the axis of rotation of the rotational device or to the central axis of rotation of the device having central axis of rotation, is arranged at a defined position of the devices used according to the invention, preferably all access openings arranged proximally to the axis of rotation, in particular to the axis of rotation of the rotational device or to the central axis of rotation of the device having central axis of rotation, are arranged at defined positions of the devices used according to the invention. The at least one access opening arranged proximally to the axis of rotation, in particular to the axis of rotation of the rotational device or to the central axis of rotation of the device having central axis of rotation, is preferably located on one of the hole positions of a micro-titration plate, preferably a 96-well plate, preferably 384-well plate. All access openings arranged proximally to the axis of rotation, in particular to the axis of rotation of the rotational device or to the central axis of rotation of the device having central axis of rotation, are preferably located on hole positions of a micro-titration plate, preferably a 96-well plate, preferably a 384-well plate. According to this embodiment, an automated filling of the at least one access opening arranged proximally to the axis of rotation, in particular to the axis of rotation of the rotational device or to the central axis of rotation of the device having central axis of rotation, by means of a pipetting robot is advantageously possible.

The devices used in the present case for cultivating cells are also devices for producing cell complexes. The term cell complex is also understood in the present case as a tissue, in particular microscopic tissue, tissue complex, organ, or organ equivalent. The term cell complex is in particular also understood as a cell complex having high cell density and three-dimensional extension.

In particular, the devices used according to the invention represent microfluidic devices, in particular cell culture systems, in particular microfluidic cell culture systems, in particular organ-on-a-disk systems, in particular microfluidic organ-on-a-disk systems.

In conjunction with the present invention, a central region of the device is a region immediately surrounding the central axis of rotation. It can preferably be an area within a preferably circular circumference having radius $r_z$ (radius of the central region)=¼ r bis ¹⁄₁₀ r of the carrier plate unit originating from the central point of the device, which is circular seen in a top view. In particular, the radius of the central region ($r_z$) of the carrier plate unit is at least $r_z$=¹⁄₁₀ r of the carrier plate unit and at most $r_z$=¼ r of the carrier plate unit.

In one preferred embodiment, the central region of the device preferably used according to the invention has at least one connecting device for a rotational device enabling a rotation of the device, for example, an external rotational drive, for example, a motor. The connecting device is in particular at least one through opening, for example, 2, 3, 4, 5, or 6 through openings, or at least one anchoring device, for example, 2, 3, or 4 anchoring devices. The connecting device, in particular the at least one through opening or at least one anchoring opening, is used for fastening the device according to the invention on a rotational device enabling a rotation, which can set the device according to the invention into rotation.

The through opening is preferably a hole, hub, or thread or a part thereof. The anchoring device is preferably a plug, flap, catch, snap, or clamp connecting device or a part thereof.

It can also be provided that the devices used according to the invention have at least one, preferably peripherally arranged, locking device for a rotational device. This locking device can be, for example, at least one clamp, which clamps the device used according to the invention on its edge, in particular its outermost edge.

It can be provided according to the invention that the devices are fastened on the rotational device with the aid of the at least one connecting device of the central region, if provided, and/or with the aid of the at least one peripherally arranged locking device. Furthermore, it is possible according to the invention that the devices used according to the invention do not themselves have a connecting or locking device, but rather the rotational device has a fixing device for the devices used according to the invention. This fixing device can be a receptacle of the rotational device adapted to the circumference of the devices used according to the invention.

In one preferred embodiment of the devices used according to the invention, the at least one channel which connects the at least one access opening to the at least one cultivation chamber, is an unbranched channel. However, according to the invention, the channel can preferably also be a singly, multiply, or frequently branched channel and connects at least one access opening to at least two cultivation chambers, in particular in a parallel arrangement of the channels and cultivation chambers to one another. This enables the parallel, simultaneous filling of multiple cultivation chambers with cells through one access opening. In one preferred embodiment, the branched channel connects at least one access opening to at least three cultivation chambers, preferably to at least four cultivation chambers, preferably to at least five cultivation chambers, preferably to at least six cultivation chambers, preferably to at least seven cultivation chambers, preferably to at least eight cultivation chambers, preferably to at least nine cultivation chambers, preferably to at least ten cultivation chambers, preferably to at least 11 cultivation chambers, preferably to at least 12 cultivation chambers, preferably to at least 13 cultivation chambers, preferably to at least 14 cultivation chambers, preferably to at least 15 cultivation chambers, preferably to at least 20 cultivation chambers, preferably to at least 25 cultivation chambers, preferably to at least 30 cultivation chambers, preferably to at least 35 cultivation chambers, preferably to at least 40 cultivation chambers, preferably to at least 45 cultivation chambers, preferably to at least 50 cultivation chambers, preferably to at least 60 cultivation chambers, preferably to at least 70 cultivation chambers, preferably to at least 80 cultivation chambers, preferably to at least 90 cultivation chambers, preferably to at least 100 cultivation chambers, preferably in each case in parallel arrangement of the channels and cultivation chambers to one another.

In one preferred embodiment of the devices used according to the invention, the at least one channel is a branched or unbranched channel which connects the at least one access opening to at least two cultivation chambers, preferably to at least three cultivation chambers, preferably to at least four cultivation chambers, preferably to at least five cultivation chambers, preferably to at least six cultivation chambers, preferably to at least seven cultivation chambers, preferably to at least eight cultivation chambers, preferably to at least nine cultivation chambers, preferably to at least ten cultivation chambers, preferably to at least 11 cultivation chambers, preferably to at least 12 cultivation chambers, preferably to at least 13 cultivation chambers, preferably to at least 14 cultivation chambers, preferably to at least 15 cultivation chambers, preferably to at least 20 cultivation chambers, preferably to at least 25 cultivation chambers, preferably to at least 30 cultivation chambers, preferably to at least 35 cultivation chambers, preferably to at least 40 cultivation chambers, preferably to at least 45 cultivation chambers, preferably to at least 50 cultivation chambers, preferably to at least 60 cultivation chambers, preferably to at least 70 cultivation chambers, preferably to at least 80 cultivation chambers, preferably to at least 90 cultivation chambers, preferably to at least 100 cultivation chambers, preferably in each case in parallel arrangement of the channels and cultivation chambers to one another.

The at least one channel which connects the at least one access opening to the at least one cultivation chamber, preferably to the at least two cultivation chambers, can in one preferred embodiment have a width of 10 to 1000 μm, preferably 10 to 800 μm, preferably 10 to 600 μm, preferably 10 to 500 μm, preferably 10 to 400 μm, in particular 50 to 150 μm, in particular 70 μm. In one particularly preferred embodiment, the at least one channel has a height of 10 to 400 μm, in particular 50 to 150 μm, in particular 70 μm. In one particularly preferred embodiment, the at least one channel can be branched, preferably in the radial directions, and in particular can have 0 to 10, preferably 1, 2, 3, 4, 5, or 6 branches. The channel height and/or the channel width can particularly preferably increase with the number of the branches.

In one particularly preferred embodiment of the present invention, the channel of the devices used according to the invention has at least over a part of its length at least two, preferably at least three, preferably at least four, preferably at least five, preferably at least six, preferably at least seven, preferably at least eight, preferably at least nine, preferably at least ten, preferably at least 11, preferably at least 12, preferably at least 13, preferably at least 14, preferably at least 15, preferably at least 20, preferably at least 25, preferably at least 30, preferably at least 35, preferably at least 40, preferably at least 45, preferably at least 50, preferably at least 60, preferably at least 70, preferably at least 80, preferably at least 90, preferably at least 100 cultivation chambers directly adjoining the channel.

In one particularly preferred embodiment of the present invention, the cultivation chambers directly adjoining the channel are arranged in parallel to one another at least over a part of the length of the channel.

In one further preferred embodiment of the present invention, the at least one channel is curved at least over a part of its length. The at least one channel preferably has a static curvature at least over part of its length. The at least one channel preferably has an angle-dependent curvature at least over a part of its length. In one particularly preferred embodiment, the at least one channel is curved at least over a part of its length by a defined angle in relation to the direction of the centrifugal force generated by rotation. In one particularly preferred embodiment of the present invention, the curvature of the at least one channel decreases from the at least one access opening arranged proximally to the axis of rotation, in particular to the axis of rotation of the rotational device or to the central axis of rotation of the device having central axis of rotation, in the direction of the at least one cultivation chamber arranged distally to the axis of rotation, in particular to the axis of rotation of the rotational device or to the central axis of rotation of the device having central axis of rotation. The curvature of the at least one channel preferably decreases continuously from the at least one access opening arranged proximally to the axis of rotation, in particular to the axis of rotation of the rotational device or to the central axis of rotation of the device having central axis of rotation, in the direction of the at least one cultivation chamber arranged distally to the axis of rotation, in particular to the axis of rotation of the rotational device or to the central axis of rotation of the device having central axis of rotation.

In one particularly preferred embodiment, the at least one access opening has a diameter of 0.2 to 20 mm, preferably 0.5 to 10 mm, preferably 1 to 8 mm, in particular 3 mm.

In one particularly preferred embodiment of the present invention, the device used according to the invention has a connecting region between the at least one access opening arranged proximally to the axis of rotation, in particular to the axis of rotation of the rotational device or to the central axis of rotation of the device having central axis of rotation, and the at least one channel. The connecting region preferably extends falling diagonally from the at least one access opening arranged proximally to the axis of rotation, in particular to the axis of rotation of the rotational device or to the central axis of rotation of the device having central axis of rotation, to the at least one channel. With the aid of such a connecting region extending diagonally falling it is advantageously possible to ensure an improved flow of the cells introduced through the at least one access opening into the carrier plate unit, in particular the cell suspension, possibly also cell culture, from the at least one access opening arranged proximately to the axis of rotation, in particular to the axis of rotation of the rotational device or to the central axis of rotation of the device having central axis of rotation, via the connecting region to the at least one channel.

In one preferred embodiment, the at least one access opening is designed as a loading chamber which has at least two access openings. Due to the design of the at least one access opening as a loading chamber, it is advantageously possible to improve the loading efficiency of the device according to the invention. In this case, the loading chamber has at least two access openings via which a flow can preferably be generated inside the loading chamber. It is possible by way of the loading chamber to increase the number of the cells actually transported into the at least one cultivation chamber during rotation of the device according to the invention.

In one particularly preferred embodiment, the at least one cultivation chamber in round form has a horizontal diameter of 0.05 to 10 mm, preferably 0.1 to 9 mm, preferably 0.2 to 8 mm, in particular 2 mm. In one particularly preferred embodiment, the radial distance ($r_2$) of the cultivation chambers from the center point of the device, in particular from the central axis of rotation of the device having central axis of rotation, is 1 to 30 cm, preferably 1 to 20 cm, preferably 2 to 15 cm, in particular 4.5 cm. The ratio of $a(\omega)$ can advantageously be set via the radial distance ($r_2$) of the cultivation chambers from the center point of the device, in particular from the central axis of rotation of the device having central axis of rotation, or the radial distance ($r_2$) of the cultivation chambers from the axis of rotation of the rotational device, respectively.

In one particularly preferred embodiment, the at least one cultivation chamber in dumbbell form has a web distance of 0.3 to 10 mm, preferably 1 mm. The web width is 50 µm to 500 µm, preferably 150 µm. The two ends have a widening perpendicular to the web of 100 µm to 2 mm, preferably 550 µm. The widening occurs abruptly at 90° or increases in a trapezoidal shape at an arbitrary angle between 0° and 90°, preferably 42°. The ends have a radial extension of 100 µm to 1 mm, preferably 300 µm. To ensure a uniform filling of the chambers in dumbbell form, the side oriented distally to the axis of rotation, in particular to the axis of rotation of the rotational device or to the central axis of rotation of the device having central axis of rotation, is rounded in one preferred embodiment.

In one particularly preferred embodiment, the at least one cultivation chamber in rectangular form has a width of 0.05 to 10 mm, preferably 500 µm, and a height of 0.05 to 10 mm, preferably 1500 µm.

In one particularly preferred embodiment, the height of the carrier plate unit, in particular the first carrier plate, is 0.8 to 20 mm, preferably 1.5 to 4 mm, in particular 1.7 to 2.5 mm, in particular 2 mm. The height of the first carrier plate should preferably correspond to the channel height plus at least one-half millimeter, preferably one millimeter, to ensure a sufficient stability of the device.

The at least one cultivation chamber can preferably be formed as round, elliptical, rectangular, trapezoidal, dumbbell-shaped, in the form of a circular segment or circular sector, and parts or combination of the mentioned forms.

In one particularly preferred embodiment, the carrier plate unit is embodied in one piece.

In one particularly preferred embodiment, the device used according to the invention is the carrier plate unit. In one particularly preferred embodiment, the device used according to the invention, in particular the carrier plate unit, is a carrier plate, in particular the first carrier plate, i.e., the carrier plate in which the cultivation of cells takes place and which is distinguished by the presence of the at least one access opening, the at least one cultivation chamber, and the at least one channel connecting the at least one access opening and the at least one cultivation chamber.

The at least one access opening formed in the carrier plate, in particular the first carrier plate, the at least one cultivation chamber, and the at least one channel connecting the at least one access opening and the at least one cultivation chamber are integrated in the carrier plate unit, in particular in the first carrier plate, or arranged on its surface, and, in one preferred embodiment, are completely or partially open in a horizontal surface of the carrier plate, i.e., each have base and wall parts in the carrier plate unit, in particular in the carrier plate, and an opening in the horizontal surface.

In conjunction with the present invention, the horizontal surface of the carrier plate unit, in particular the first carrier plate, which has the opening of the at least one cultivation chamber, is denoted as the upper or upwardly facing surface of the first carrier plate or the carrier plate unit.

In one particularly preferred embodiment, the carrier plate unit, in particular the first carrier plate, can be completely or partially terminated facing upward by a preferably reversibly applicable cover, or a layer, for example, a PDMS layer, so that at least the at least one cultivation chamber and the at least one channel are closed fluid-tight to the outside. The at least one access opening can preferably be designed as reversibly closable to enable filling with cells and/or culture medium and subsequent closing. The at least one access opening can optionally also be arranged on the lower horizontal surface arranged opposite to the upper horizontal surface of the carrier plate unit, in particular the first carrier plate.

In one preferred embodiment, the carrier plate unit comprises, in particular the carrier plate unit consists of at least two carrier plates, in particular a first and a second carrier plate, which are provided as separate components and, after reversible or irreversible joining together in one preferred embodiment arranged one over another, preferably congruent with one another, form a carrier plate unit. In one preferred embodiment, the device used according to the invention, in particular the carrier plate unit, thus comprises at least one first carrier plate, in particular for the cultivation of cells, and at least one second carrier plate, which is arranged above or below it after joining together of both carrier plates and connected thereto, preferably fluid-tight to the outside, in particular for supplying the cells located in the cultivation chamber with culture medium.

In this embodiment, the first carrier plate has the at least one access opening, the at least one cultivation chamber, and the at least one channel connecting the at least one access opening and the at least one cultivation chamber. According to the invention, the second carrier plate arranged on the first carrier plate, preferably so it is fluid-tight to the outside, preferably has at least one media opening accessible from outside the carrier plate unit, at least one media chamber, and at least one media channel connecting the at least one media opening to the at least one media chamber, wherein the at least one media chamber has an opening, in particular an opening which enables a fluidic connection to the at least one cultivation chamber of the first carrier plate arranged below or above the second carrier plate after joining together of both carrier plates, and wherein the media opening is embodied as an inlet or outlet for media, in particular as an opening accessible from outside the carrier plate unit. The at least one media opening is preferably arranged on the upper horizontal surface of the second carrier plate facing away from the first carrier plate. The at least one media opening, the at least one media chamber, and the at least one media channel connecting the at least one media opening and the at least one media chamber are integrated into the second carrier plate or arranged on its surface, and, in one preferred embodiment, completely or partially open in a horizontal surface of the carrier plate, i.e., they each have base and wall parts in the carrier plate and an opening in the horizontal surface.

In one preferred embodiment, the second carrier plate has at least two media openings, in particular at least one media inlet and at least one media outlet, which are connected to one another via at least one media channel and at least one media chamber. The at least one media channel preferably connects at least two media openings to at least one, preferably at least two media chambers.

In one particularly preferred embodiment, the at least one access opening of the carrier plate unit, in particular the first carrier plate, can be located in the horizontal surface of the first carrier plate facing downward and away from the second carrier plate. In one preferred embodiment, the at least one media channel can, like the at least one media chamber, be provided in the lower horizontal surface facing toward the first carrier plate after joining together of the two carrier plates and after joining together with the first carrier plate can preferably be in fluidic connection to the at least one channel located underneath it and the at least one cultivation chamber located underneath it.

In one particularly preferred embodiment, however, the first carrier plate can also be arranged above the second carrier plate or can possibly be arranged between carrier plates having two media openings, media channels, and media chambers.

It can also preferably be provided according to the invention that only the media chamber of the second carrier plate has a fluidic connection to the cultivation chamber of the first carrier plate and the channels of the first carrier plate and the media channels of the second carrier plate are each provided fluid-tight and are possibly also not formed overlapping with one another.

If in one preferred embodiment according to the invention at least two carrier plates, in particular a first and a second carrier plate, are provided, the second carrier plate, after joining together with the first carrier plate, covers the upwardly oriented openings of the at least one cultivation chamber and the at least one channel provided in its upper surface and of the at least one channel and possibly the at least one access opening on top, preferably in a fluid-tight manner, wherein the at least one cultivation chamber of the first carrier plate and the at least one media chamber of the second carrier plate are fluidically connected to one another.

In one preferred embodiment, it is provided that a passage for the access opening of the first carrier plate arranged below the second carrier plate after joining together of the two carrier plates is embodied in the at least one second carrier plate. This passage can be designed as reversibly closable.

It is thus particularly preferable according to the invention that the at least one cultivation chamber of the first carrier plate and the at least one media chamber of the second carrier plate are arranged overlapping with one another and are fluidically connected to one another. The cells located in the cultivation chambers can thus be supplied with nutrients via the media opening, the media channel, and the media chamber, in particular by supplying cell culture medium. Furthermore, therapeutic, pharmaceutical, or cosmetic preparations and substances can preferably be administered to the cells via the media openings, media channels, and media chambers formed in the second carrier plate. This advantageously enables simple testing of the therapeutic effectiveness or toxicity of the substances on the cells or tissue complexes in the cultivation chambers.

In one particularly preferred embodiment, it can thus be provided that the first carrier plate has at least one access opening, at least one cultivation chamber, and at least one channel connecting the at least one access opening to the at least one cultivation chamber, and this first carrier plate is used for cultivating cells, in particular for producing cell complexes, in particular tissues, and the second carrier plate arranged, preferably fluid-tight, on the first carrier plate is used for the supply of the cultivated cells and in particular has at least one media opening, at least one media chamber, and at least one media channel connecting the at least one media opening to the at least one media chamber, and wherein both the media opening and also the access opening are embodied as openings accessible from outside the carrier plate unit and at least the at least one cultivation chamber overlaps with the at least one media chamber and they are fluidically connected to one another, so that a supply of the cultivation chamber with medium through the media chamber is enabled. In one preferred embodiment, the at least one media channel can also be embodied as overlapping and in fluidic connection to the at least one channel connecting the at least one access opening to the at least one cultivation chamber.

In one particularly preferred embodiment, it can also be provided that the first carrier plate unit has at least one access opening arranged proximally to the axis of rotation, in particular to the axis of rotation of the rotational device or to the central axis of rotation of the device having central axis of rotation, at least one cultivation chamber arranged distally to the axis of rotation, in particular to the axis of rotation of the rotational device or to the central axis of rotation of the device having central axis of rotation, and at least one channel connecting the at least one access opening to the at least one cultivation chamber, and this first carrier plate is used for cultivating cells, in particular for producing cell complexes, in particular tissues, and the second carrier plate arranged, preferably fluid-tight, on the first carrier plate is used for the supply of the cultivated cells and in particular has at least one media opening, at least one media chamber, and at least one media channel connecting the at least one media opening to the at least one media chamber, and wherein both the media opening and also the access opening are embodied as openings accessible from outside the carrier plate unit and at least the at least one cultivation chamber overlaps with the at least one media chamber and they are fluidically connected to one another, so that a supply of the cultivation chamber with medium through the media chamber is enabled. In one preferred embodiment, the at least one media channel can also be embodied as overlapping and in fluidic connection to the at least one channel connecting the at least one access opening to the at least one cultivation chamber.

In one preferred embodiment, the at least one media channel of the second carrier plate, which connects the at least one media opening to the at least one media chamber, is an unbranched media channel. According to the invention, the media channel can preferably also be a singly, multiply, or frequently branched media channel and connects at least one media opening, preferably at least two media openings, in parallel or in series to at least two media chambers. This enables the parallel filling of multiple media chambers with cell culture medium, pharmaceutical or cosmetic substances or the like through one media opening. In one preferred embodiment, the branched media channel connects at least one media opening to at least three media chambers, preferably to at least four media chambers, preferably to at least five media chambers, preferably to at least six media chambers, preferably to at least seven media chambers, preferably to at least eight media chambers, preferably to at least nine media chambers, preferably to at least ten media chambers, preferably to at least 11 media chambers, preferably to at least 12 media chambers, preferably to at least 13 media chambers, preferably to at least 14 media chambers, preferably to at least 15 media chambers, preferably to at least 20 media chambers, preferably to at least 25 media chambers, preferably to at least 30 media chambers, preferably to at least 35 media chambers, preferably to at least 40 media chambers, preferably to at least 45 media chambers, preferably to at least 50 media chambers, preferably to at least 60 media chambers, preferably to at least 70 media chambers, preferably to at least 80 media chambers, preferably to at least 90 media chambers, preferably to at least 100 media chambers, in each case in parallel arrangement of the media channels and media chambers in relation to one another.

In one particularly preferred embodiment, the at least one media channel of the second carrier plate, which connects the at least one media opening to the at least one media chamber, does not have a section extending perpendicularly to the direction of the centrifugal force generated by rotation. According to this embodiment, air inclusions can advantageously be prevented and an optimum media supply can be ensured by rotation.

In one preferred embodiment, it can also be provided that the at least one media channel connects at least one media opening to at least two or more media chambers, which are arranged in series. This means the at least one media channel connects the at least two media chambers in series. Furthermore, it can be provided that the at least one media channel connects at least two media openings to at least one, preferably at least two, three, four, five, six, seven, eight, nine, or ten media chambers, which are arranged in series. It can be provided in this case that one of the at least two media openings functions as a media inlet and a second one as a media outlet, so that the medium, in particular the culture medium, can flow through the media channel, and in particular circulate. The culture medium preferably flows through the media channel continuously or in pulses. It can furthermore be provided that pumps, pressure gradients, or the like are provided or integrated or the rotation of the device is used to enable a flow of the medium. In these embodiments, the at least one media channel does connect at least two media openings to at least two or more media chambers, but is not a branched media channel.

It can also be provided according to the invention that a second carrier plate has branched media channels, which connect at least one or at least two media openings to at least two media chambers in parallel, and unbranched media channels, which connect at least one or at least two media openings to at least two media chambers in series.

In one particularly preferred embodiment, the width of the at least one media channel is 5 to 600 µm, preferably 10 to 400 µm, preferably 50 to 150 µm, in particular 70 µm. In one particularly preferred embodiment, the height of the at least one media channel is 5 to 600 µm, preferably 10 to 400 µm, preferably 50 to 150 µm, in particular 70 µm. In one particularly preferred embodiment, the at least one media channel can be branched, in particular can have 0 to 10, preferably 1, 2, 3, 4, 5, or 6 branches. The media channel height and/or the media channel width can particularly preferably increase with the number of the branches.

In one particularly preferred embodiment, the diameter of the at least one media opening is 0.5 to 20 mm, preferably 0.7 to 10 mm, preferably 1 to 8 mm. In conjunction with the height of the second carrier plate, this enables the introduction of 1 to 200 cm, preferably 2 to 100 µl, in particular 5 to 50 µl media volume.

In one particularly preferred embodiment, the at least one media chamber in round form has a horizontal diameter of 0.1 to 10 mm, preferably 0.2 to 8 mm, in particular 2 mm. In one particularly preferred embodiment, the radial distance of the media chambers to the center point, in particular the radial distance of the media chambers to the central axis of rotation of the device having central axis of rotation, is 1 to 20 cm, preferably 2 to 10 cm, in particular 4.5 cm.

In one preferred embodiment of the present invention, the at least one media chamber can be embodied as round, elliptical, rectangular, trapezoidal, dumbbell-shaped, in the form of a circular segment or circular sector, and parts or combinations of the mentioned forms.

It can also be provided according to the invention that the second carrier plate has one or more integrated or external pumps which ensure the medium supply.

In one particularly preferred embodiment, the height of the second carrier plate is 0.8 to 20 mm, preferably 1.5 to 4 mm, in particular 1.7 to 2.5 mm, in particular 2 mm. The height of the second carrier plate is preferably to correspond to the media channel height plus at least one-half millimeter, preferably one millimeter, to ensure a sufficient stability of the device.

At least one separating device, in particular a membrane, is particularly preferably arranged between the first carrier plate and the second carrier plate. In one preferred embodiment, the separating device is thinner than the first and second carrier plate. The separating device, in particular membrane, is preferably similar to endothelium and/or porous. In one preferred embodiment, the separating device enables a diffusive material exchange between the first and the second carrier plate, in particular between the at least one media chamber of the second carrier plate and the at least one cultivation chamber of the first carrier plate. In one preferred embodiment, it can be provided that a membrane is applied in each case between a cultivation chamber and a media chamber or a single membrane in carrier plate size or in ring shape or arbitrarily large subsections thereof in the width of the media and/or cultivation chambers is used. The at least one separating device, in particular membrane, is preferably produced from PET (polyethylene terephthalate), PC (polycarbonate), glass, PDMS (polydimethyl siloxane), or a negative resist material, in particular epoxy photoresist (SU-8 or 1002F-50). The separating device, in particular membrane, can preferably also be produced from polyolefins, polystyrene, "cell culture treated" polystyrene, polyalkyl methacrylate and polyalkyl acrylate, polyacrylamide, polycarbonate, polyethylene glycol, poly(N-isopropylacrylamide), polyacrylonitrile, polyvinyl acetate, polyvinyl alcohols, polyvinyl chloride, polyoxymethylene, polyamide, polyimide, polyurethane, polyvinylidene fluoride (PVDF), phenols, amino epoxy resins, polyester, polyether, polyethylene terephthalate (PET), polyglycolic acids (PGA) and other degradable polyesters, poly-(p-phenylene terephthalamide), polyphosphazene, polypropylene, and silicone elastomers, and also copolymers and combinations thereof. In one embodiment, the membrane can also be degradable, in particular biodegradable.

The separating device particularly preferably has a precise, defined structure, biological compatibility, and low autofluorescence in order to enable an optical examination of the cultivated tissue. The separating device may advantageously be individualized depending on the application and also cell type to be cultivated, i.e., the pore size, porosity, and arrangement of the pores can be adapted. It is preferable for the pores to be smaller than the cells used so as not to flush them out of the cultivation chambers.

In one preferred embodiment, a hexagonal grid having a porosity of 1-20%, preferably 5 to 10%, and a pore size of 1-5 µm, preferably 4 µm, is used for the separating device (see FIG. 10). The permeable pores are particularly preferably only located in the overlap of cultivation chamber and media chamber to ensure the diffusion only in this region.

In one particularly preferred embodiment, the height of the device used according to the invention, in particular of the device having a first carrier plate, a separating device, and a second carrier plate, is 2 to 40 mm, preferably 2 to 30 mm, preferably 2 to 20 mm, preferably 2 to 10 mm, in particular 2 to 5 mm.

In a further preferred embodiment of the present invention, the carrier plate unit of the devices used according to the invention comprises a reservoir for liquids, in particular for cell culture medium or active ingredients to be studied.

In addition to the first carrier plate, preferably in addition to the first and second carrier plate, the carrier plate unit preferably comprises a reservoir for liquids, in particular for cell culture medium or active ingredients to be studied.

The carrier plate unit preferably comprises a first carrier plate, a second carrier plate preferably arranged above the first carrier plate, and a reservoir preferably arranged above the second carrier plate for liquids, in particular for cell culture medium or active ingredients to be studied.

In one particularly preferred embodiment of the present invention, the reservoir has at least one container, preferably a media container, arranged proximally to the axis of rotation, in particular to the axis of rotation of the rotational device or to the central axis of rotation of the device having central axis of rotation.

In a further preferred embodiment of the present invention, the reservoir has at least one separate container, preferably a media container, arranged proximally to the axis of rotation, in particular to the axis of rotation of the rotational device or to the central axis of rotation of the device having central axis of rotation, and at least one separate container, preferably a media container, arranged distally to the axis of rotation, in particular to the axis of rotation of the rotational device or to the central axis of rotation of the device having central axis of rotation, wherein the container, preferably media container, arranged proximally to the axis of rotation, in particular to the axis of rotation of the rotational device or to the central axis of rotation of the device having central axis of rotation, and the container, preferably media container, arranged distally to the axis of rotation, in particular to the axis of rotation of the rotational device or to the central axis of rotation of the device having central axis of rotation, have a fluid connection to one another.

The at least one separate container, preferably media container, arranged proximally to the axis of rotation, in particular to the axis of rotation of the rotational device or to the central axis of rotation of the device having central axis of rotation, preferably comprises at least one media opening, preferably at least one media outlet.

The at least one separate container, preferably media container, arranged distally to the axis of rotation, in particular to the axis of rotation of the rotational device or to the central axis of rotation of the device having central axis of rotation, preferably comprises at least one media opening, preferably at least one media inlet.

According to one preferred embodiment, a liquid, preferably cell culture medium, located in the separate container, preferably media container, arranged proximally to the axis of rotation, in particular to the axis of rotation of the rotational device or to the central axis of rotation of the device having central axis of rotation, is supplied upon rotation of the carrier plate unit around the axis of rotation, in particular to the axis of rotation of the rotational device or to the central axis of rotation of the device having central axis of rotation, through the at least one media opening, preferably through the at least one media outlet, of the container arranged proximally to the axis of rotation, in particular to the axis of rotation of the rotational device or to the central axis of rotation of the device having central axis of rotation, to the fluidically connected media opening, preferably the fluidically connected media inlet, of the second carrier plate and conveyed via at least one unbranched or branched media channel located in the second carrier plate unit to the at least one media opening, preferably to the at least one media outlet of the second carrier plate. The liquid, preferably the cell culture medium, is supplied from the at least one media opening, preferably the at least one media outlet of the second carrier plate, via the at least one fluidically connected media opening, preferably the at least one fluidically connected media inlet, of the at least one separate container, preferably media container, arranged distally to the axis of rotation, in particular to the axis of rotation of the rotational device or to the central axis of rotation of the device having central axis of rotation. By way of the preferably continuous or pulsed flow of liquid, preferably cell culture medium, from the container, preferably media container arranged proximally to the axis of rotation, in particular to the axis of rotation of the rotational device or to the central axis of rotation of the device having central axis of rotation, to the container, preferably media container, arranged distally to the axis of rotation, in particular to the axis of rotation of the rotational device or to the central axis of rotation of the device having central axis of rotation, via the media channel and the media chambers of the second carrier plate, a supply of the cells located in the at least one cultivation chamber of the first carrier plate with liquid, preferably cell culture medium, can be ensured.

In this manner, it is advantageously possible to supply the cells located in the at least one cultivation chamber of the device according to the invention, preferably continuously or in pulses, with larger quantities of liquid, preferably cell culture medium.

In one preferred embodiment, the carrier plate unit, in particular the first and/or second carrier plate, preferably the first and/or second carrier plate and/or the reservoir, is constructed from glass or polymer material. The carrier plate unit is particularly preferably constructed from a polymer material, for example, PDMS (polydimethyl siloxane), PMMA (polymethyl methylacrylate), PVC (polyvinylchloride), COC (cycloolefin copolymers), PS (polystyrene), PC (polycarbonate), polyimide, polyurethane, PET (polyethylene terephthalate), polyester, in particular polycaprolactone (PCT), or combinations thereof.

The present invention furthermore relates to methods for producing cell complexes, wherein the cells are preferably human or animal cells, in particular cell suspensions of such cells.

In particular, the cultivation of the cells in the device according to the invention is performed by: a) providing the cells, possibly in the form of suspensions, for example, in cell culture medium, cross-linked or non-cross-linked hydrogel, and a device according to the invention, b) introducing the cells, possibly in the form of suspensions, for example, in cell culture medium, cross-linked or non-cross-linked hydrogel, into the device according to the invention through the at least one access opening, c) introducing the device according to the invention into a rotational device enabling a rotation, d) setting the device according to the invention into rotation, e) receiving cells in the at least one cultivation chamber, and f) cultivating the cells in the at least one cultivation chamber. It can also be provided according to the invention that step c) is carried out before step b). A cell complex, tissue complex, or a cell culture having particularly high cell density particularly preferably results due to the cultivation of the cells in the at least one cultivation chamber.

In one particularly preferred embodiment, the device used according to the invention is firstly activated in $O_2$ plasma before use, to achieve better wetting of the channels and/or media channels upon filling. In particular, 500 W, 60 seconds, and 1 mbar are used as parameters.

In the method according to the invention for cultivating cells, in particular for producing cell complexes, it can preferably also be provided that before carrying out method step b), in a method step x) an introduction of cell culture medium through the at least one access opening is provided, which is subsequently transported in a method step y) by rotation, i.e., the centrifugal force, through the at least one channel connecting the at least one access opening to the at least one cultivation chamber into the cultivation chamber. This causes a removal of air bubbles, which have an interfering effect during the cultivation of the cells. Subsequently, it is preferably provided according to the invention that method steps b) to d), in particular b) to f) are carried out.

Furthermore, the method steps g) introducing cell culture in into the at least one media opening, h) setting the device into rotation, and i) receiving cell culture in the at least one media chamber to supply the cells in the cultivation chamber are preferably carried out according to the invention.

In a further preferred embodiment of the present invention, the method for cultivating cells, in particular for producing cell complexes, comprises in method step g) the introduction of cell culture medium into the at least one separate container, preferably media container, of the reservoir arranged proximally to the centrally located axis of rotation of the carrier plate unit, h) setting the device into rotation, and i) receiving cell culture medium in the at least one media chamber to supply the cells in the cultivation chamber.

In particular, in this case a continuous or pulsed flow through the media channels and media chambers with cell culture medium is enabled by the generation of a pressure gradient, external or integrated pumps, or by rotation of the device.

The cell culture medium used for the cultivation of the cells is preferably adapted for the cell species used, for example, for fibroblasts DMEM with 10% FBS and 1% penicillin/streptomycin is used. The cell culture medium can optionally contain biomolecules for cell adhesion. In particular, in step x), cell culture medium is pipetted into the access openings, wherein the volume is adapted to the cultivation chamber volume depending on the device geometry. A volume of 1-40 in particular 10-20 µl cell culture medium is preferably introduced into the access opening(s) and subsequently transported in method step y) by rotation into the cultivation chambers.

In method step b), the cells, in particular the cells provided in cell culture medium or hydrogel, are introduced into the access openings, wherein the cell concentration is adapted to the cultivation chamber volume and desired filling proportion, and also the cell type used and the more specific cell geometry. According to the invention, 1-40 µl, in particular 10-20 µl cell culture medium or hydrogel having a cell concentration of $10^3$ to $10^8$, in particular $10^4$-$10^7$/10 µl are preferably introduced into the access opening.

In one preferred embodiment, the introduction of cell culture medium, hydrogel, and cells is performed by pipetting, injecting, or other suitable methods.

In one particularly preferred embodiment it can be provided that after method step e), the at least one media chamber and thus also the at least one cultivation chamber fluidically connected to the at least one media chamber are supplied with medium via the at least one media opening and a particularly preferred cultivation is carried out. This method step can preferably be carried out after ending the rotation, so that it is preferably provided in particular that a medium supply and cultivation of the cells is carried out at a standstill of the device according to the invention. Furthermore, it can also be provided according to the invention that the rotation is utilized for the medium supply and the cultivation of the cells, i.e., step f) of the method according to the invention, thus takes place in rotation.

In one preferred embodiment of the present invention it can be provided that after method step e), the at least one media chamber and thus also the at least one cultivation chamber fluidically connected to the at least one media chamber are supplied with medium via the at least one media opening, preferably the at least one media outlet, of the at least one separate container, preferably media container, arranged proximally to the axis of rotation, in particular to the axis of rotation of the rotational device or to the central axis of rotation of the device having central axis of rotation, of the reservoir and the at least one media opening of the second carrier plate fluidically connected thereto and a particularly preferred cultivation is carried out. According to this embodiment, it is provided that the rotation is utilized for the medium supply and thus the cultivation of the cells, i.e., step f) of the method according to the invention, takes place in rotation.

In one particularly preferred embodiment, the rotation of the device according to the invention occurs at a speed of rotation of 0 to 4000 RPM, in particular for 0.1 to 30 minutes, in particular at 1500 to 2500 RPM, in particular for 60 to 360 seconds. These parameters apply in particular for the filling of the cultivation chambers, media chambers, channels, and media channels. If a cultivation of the cells under rotation is provided, i.e., the rotation is utilized for the medium supply of the cells, a speed of rotation of 0 to 1000 RPM, in particular 0 to 100 RPM, preferably 10 to 50 RPM is thus preferably provided.

According to the invention, a cell complex preferably results due to the cultivation of the cells in the at least one cultivation chamber of the devices used according to the invention.

The present invention therefore relates to a method for producing a cell complex, in particular a three-dimensional cell complex, characterized in that the method according to the invention for cultivating cells is carried out and a cell complex is obtained.

The present invention also relates to a method for producing a device for use according to the present invention, in particular, such a method is a method in the scope of which in a first method step at least one material, in particular polymer material, forming the carrier plate unit is provided and it is formed in a method providing shape and stability, in particular a lithographic method, preferably a soft or UV lithographic method, into a device according to the present invention.

This means that the device used according to the invention is preferably produced with the aid of photolithography, soft lithography, selective laser sintering, laser cutting and milling, laser ablation, inkjet printing using photopolymers, melt coating (thermoplastic extrusion), LOM (laminated object manufacturing), stereolithography, hot embossing, in particular micro-hot embossing, milling (CNC milling, in particular micro-milling), injection molding, in particular micro-injection molding, and/or 3D printing. These methods can be used either directly for producing the device or for producing mold templates and subsequently molding the device.

In particular, the present invention also relates to a method for producing a device for use according to the present invention, comprising the following method steps
- i) providing at least one negative resist material, at least one silicon substrate, and at least one material forming the carrier plate unit,
- ii) producing a mold template for a carrier plate unit, in particular a first carrier plate, from the negative resist material on the silicon substrate by UV lithography,
- iii) filling the mold template with the material forming the carrier plate unit,
- iv) curing the material forming the carrier plate unit in the mold template, and
- v) obtaining the carrier plate unit, in particular a first carrier plate.

The present invention also relates to an above method according to the invention for producing a device, wherein in addition method step ii) comprises the production of a mold template for a second carrier plate, wherein in addition method step iii) comprises the filling of the mold template for the second carrier plate with the material forming the carrier plate unit, in addition method step iv) comprises the curing of the material forming the carrier plate unit in the mold template for the second carrier plate, and in addition method step v) comprises obtaining a second carrier plate and subsequently joining it together with the first carrier plate.

PDMS is particularly preferably used as the material forming the carrier plate unit, poured in step iii) into the lithographically produced mold and cured for 0.5-12 hours, preferably 1-2 hours at 50-100° C., preferably 60-80° C.

In a further preferred embodiment, it is provided that in addition in method step i), the provision of at least one separating device, in particular at least one membrane is provided, and in addition in method step v), the joining together of the first carrier plate, the at least one separating device, and the second carrier plate is provided.

If lithographically produced membranes (for example, based on 1002F-50 or SU-8) are used, the first carrier plate, the membrane, and the second carrier plate are bonded to one another with the aid of $N_2$ plasma to join together the device. Bonding with the aid of $O_2$ plasma is also possible for other membrane materials.

In particular, for the joining together, either the first or the second carrier plate is firstly activated in $N_2$ plasma depending on the membrane geometry, for which preferably parameters of 30-100 W, 30-120 seconds, and 0.3-1.5 mbar are preferably used. The activated carrier plate is aligned on the membrane located on the silicon substrate, weighted with weight, and the bond is cured at 60-120° C. for 0.5-24 hours in the furnace. The combined layer made of carrier plate and membrane is subsequently detached from the silicon substrate in $H_2O$. The further carrier plate is now activated using the above-mentioned parameters in an $N_2$ plasma, aligned on the free membrane side, weighted, and the bond is cured with above-mentioned parameters in the furnace. In addition, 4 through openings are produced in the middle in the joined and cured disk for the fastening on the motor.

Further advantageous designs of the present inventions result from the dependent claims.

BRIEF DESCRIPTION OF THE DRAWINGS

The invention will be explained in greater detail on the basis of the following example and the associated figures.

In the figures:

FIG. 11 shows a device used according to the invention having first and second carrier plate (111, 112) and membrane (135) in between.

DESCRIPTION OF EXAMPLE EMBODIMENTS

Example

Production of a Device Used According to the Invention

Figure 6:
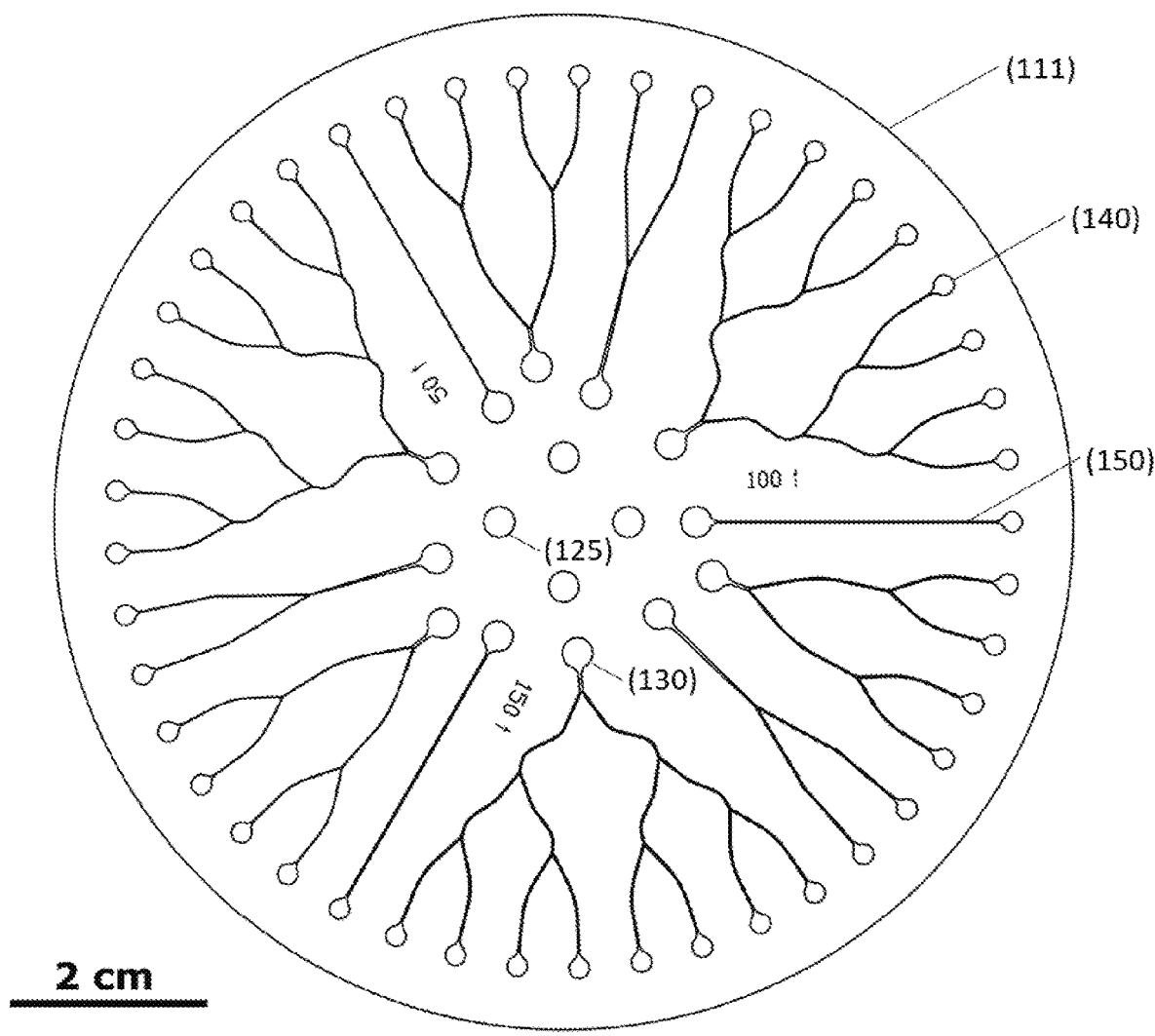
FIG. 6 schematically shows the structure of a first carrier plate (111).

The production of an exemplary organ disk is described hereafter. The disk according to the invention, i.e., the carrier plate unit, is produced from polydimethyl siloxane (PDMS, purchased from Dow Corning as Sylgard 184). The individual carrier plates are produced by soft lithography, wherein firstly a mold template of the respective carrier plate is manufactured in the required channel height on a silicon substrate (wafer) by means of UV lithography from the photoresist SU-8. The mold templates have the following properties for the described disk:

The first carrier plate of the exemplary disk contains 45 cultivation chambers arranged at a radial distance of 4.5 cm from the disk center point, i.e., the central axis of rotation, having a diameter of 2 mm. FIG. 6 shows the carrier plate design used. In addition, 4 through openings for fastening the disk on the motor are applied in the middle of the carrier plate unit. The chambers are filled via 12 access openings through channels of the height of 50 μm. In each case ⅓ of the channels connecting the access opening to the cultivation chamber has a channel width of 50 μm, 100 μm, and 150 μm. There are 4 different types of symmetrical branches per channel width: 0 branches (access opening connected directly to the chamber), 1 branch (access opening connected to 2 chambers), 2 branches (access opening connected to 4 chambers), 3 branches (access opening connected to 8 chambers). The access opening diameter and the diameter of the passage openings are 3 mm.

The second carrier plate contains media chambers which are arranged matching with the cultivation chambers of the first carrier plate. There is one media channel per media opening, which supplies all media chambers connected to the media opening. All media channels have a width of 80 μm and a height of 50 μm. Each media channel has two media openings, wherein one media opening functions as a media outlet and is located outside the channel of the first carrier plate. The media openings have a media opening diameter of 1 mm.

PDMS is firstly mixed in the ratio of 10:1 from the two components base:agent and degassed in the desiccator for 30 minutes under vacuum. 21 g PDMS are poured in each case into the lithographically produced mold template for the first and second carrier plate and cured for 14 hours at 60° C. The silicon substrate used having the structures to be molded has a diameter of 10 cm. Draining off of the PDMS is avoided by an additional acrylic ring, which is clamped on the silicon substrate, and the disk is molded to a final disk diameter of 9.5 cm. To avoid irregularities in the carrier plate thickness in the edge region of the disk, the acrylic ring is filled to the top with PDMS, which results in a height of the first and second carrier plate of 3 mm.

After the curing of the two carrier plates, the through holes preformed in the first and second carrier plate are punched out. Additional access openings having a diameter of 3 mm and media openings having a diameter of 1 mm are stamped out in the second carrier plate. Both carrier plates are now flushed out using isopropanol and dried using nitrogen. The carrier plates are additionally covered with adhesive tape, which is pulled off again to remove contaminants on the surface.

Figure 10:
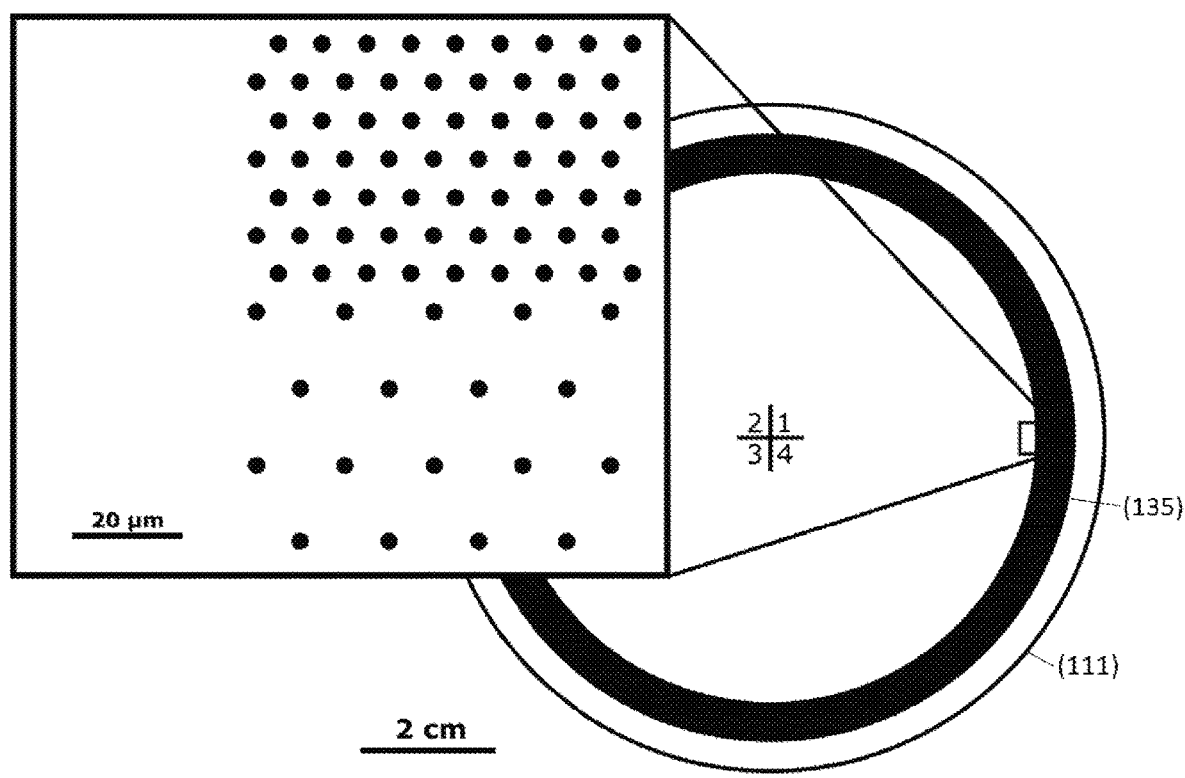
FIG. 10 schematically shows the structure of the membrane (135).

For the illustrated example, a membrane based on epoxy photoresist (1002F) is used. The membrane is produced in carrier plate size for the entire disk. The design of the membrane used for the complete disk is shown in FIG. 10. In this case, the disk membrane is divided into 4 quadrants having the pore sizes of 3 μm (I), 3 μm (II), 5 μm (III), 3 μm (IV) and the porosities 12.7% (I), 5.6% (II), 5.6% (III), 3.2% (IV). The permeable pores are seated arranged in a hexagonal grid only in the edge region, having radial distance between 4.0 and 4.6 cm, i.e., at the overlap between the cultivation chambers and the media chambers to ensure the diffusion in this region. In addition, the membrane is permeable at the point of the access openings. The approximately 10 μm thick membrane is located after the production by means of lithography in the clean room on a silicon wafer and can be detached in $H_2O$.

For the assembly of the organ disk, the individual layers are bonded to one another with the aid of $N_2$ plasma, i.e., connected to one another. For this purpose, firstly the first carrier plate is activated in $N_2$ plasma, for which parameters of 50 W, 90 seconds, and a flow of 0.2 Nl/h are used. The activated carrier plate is aligned on the membrane located on the silicon substrate, weighted using weight, and the bond is cured at 60° C. overnight, i.e., for at least 14 hours in the furnace. Subsequently, the combined layer made of carrier plate and membrane is deposited in $H_2O$ (Milli-Q ultrapure water). After approximately 5 minutes, the soap layer dissolves under the membrane, so that the combined layer can be detached from the silicon substrate. The second carrier plate is now also activated using the above-mentioned parameters in an $N_2$ plasma, aligned on the free membrane side, weighted, and the bond is cured in the furnace with the above-mentioned parameters. After this step, the disk is finished and ready for use.

Application of the Disk

In the present example, the disk is used to enrich fibroblasts in the cultivation chambers and later to cultivate them. For application of the disk, it is firstly activated in $O_2$ plasma to achieve better wetting of the channels upon filling. 50 W, 60 seconds, and an $O_2$ flow of 0.2 Nl/h are used as parameters.

10 μl of the cell culture medium for fibroblasts (DMEM with 10% FBS and 1% penicillin/streptomycin) are pipetted into the access openings. The organ disk is subsequently closed using a cover and screwed onto the motor via the through holes.

The disk is set into rotation for 3 minutes at 2000 RPM so that the channels and cultivation chambers of the first carrier plate are filled with medium.

The disk is subsequently removed from the motor again, the cover is opened, and the remaining medium volume in the access openings is suctioned off using a pipette. In the next step, the cell suspension is pipetted into the access openings. For this purpose, in the example 10 µl of a cell suspension of fibroblasts having a concentration of $10^5$ cells/10 µl are used The disk is closed again and attached to the motor. The subsequent disk rotation at 2000 RPM for three minutes conveys the decanted cells into the cultivation chambers. This corresponds to an acceleration, which is routine for the centrifugation of fibroblasts, of 200 g (g for the outer edge of the chambers at $r_2$=0.05 m: a=$5*10^{-5}$*rpm$^2$g at a speed of rotation of ω=2000 RPM).

The cultivation chambers are now filled with fibroblasts, so that the disk can be removed from the motor and used at a standstill. For this purpose, a defined medium flow is provided with the aid of external pumps via the media openings.

Production of a Cell Complex

For the production of a cell complex by means of the method according to the invention, a device having a channel (150) inclined in relation to the direction of the centrifugal force $F_C$ generated by rotation was used, along the length of which eight cultivation chambers (140) are arranged.

To deaerate the channel (150), the device was firstly rotated for the duration of 2 minutes at 200 g. A suspension containing 80,000 cardiomyocytes was subsequently placed in the access opening (130). After closing the access opening (130), the device was centrifuged for 10 minutes at 200 g, whereby the cardiomyocytes were conveyed into the cultivation chambers (140).

Figure 18:
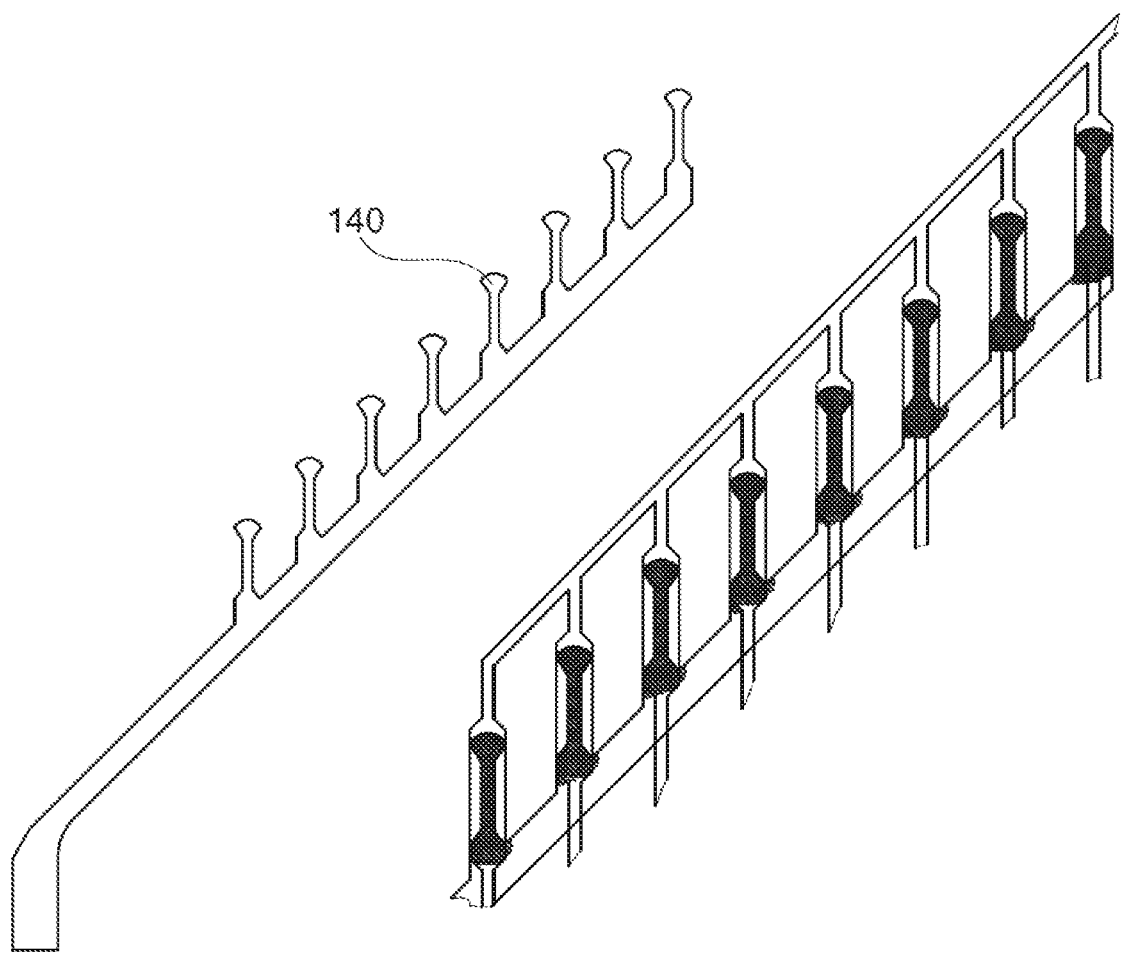
FIG. 18 shows eight cultivation chambers (140) filled with cells.

FIG. 18 shows the formation of a dense three-dimensional cell complex in the eight cultivation chambers (140) of the device. For further cultivation of the obtained cell complex, the cells in the cultivation chambers (140) were subsequently supplied with medium by an external spray pump at a flow rate of 50 µl/h.

Measurement of the Volume Flow Conveyed by Rotation

A measurement of the volume flow conveyed by rotation was performed by gravimetric measurement of the collected conveyance volume. For this purpose, the volume flow of water from a reservoir having constant fill level through a media channel of a device according to the invention was determined at different speeds of rotation (RPM) (Table 1).

TABLE 1 measured values of the gravimetric flow measurement and theoretically computed flow rates.

| Speed [rpm] | Theoretical flow [µL/h] | Average flow [µL/h] | Standard deviation [µL/h] | Number of measured values [—] |
|---|---|---|---|---|
| 100 | 64 | 86 | 7 | 12 |
| 200 | 144 | 118 | 31 | 12 |
| 300 | 277 | 214 | 35 | 9 |
| 400 | 463 | 414 | 65 | 12 |
| 500 | 702 | 715 | 69 | 12 |
| 600 | 994 | 1011 | 89 | 12 |
| 700 | 1339 | 1457 | 99 | 8 |
| 800 | 1737 | 1783 | 163 | 11 |

Figure 31:
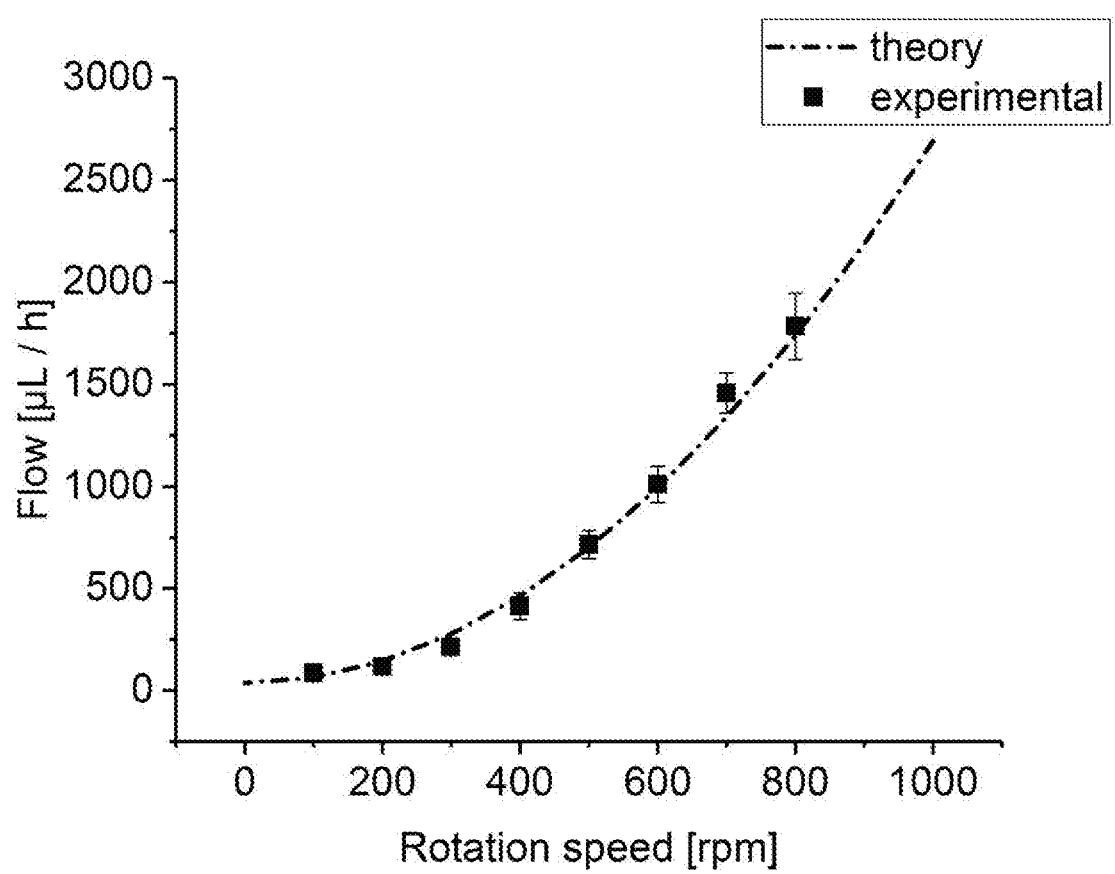
FIG. 31 shows the experimentally determined and computed volume flow in a device according to the invention as a function of the rotational velocity.

FIG. 31 illustrates that the volume flow of water determined by gravimetric measurement as a function of the speed of rotation in a device according to the invention having central axis of rotation nearly corresponds to the theoretically computed volume flows.

The experiment thus shows that it is possible using the device according to the invention having central axis of rotation to convey liquids, in particular medium, by rotation around a central axis of rotation from the at least one access opening arranged proximally to the central axis of rotation via the channel to the at least one cultivation chamber arranged distally to the central axis of rotation even without external pumps.

DESCRIPTION OF THE FIGURES

Figure 1:
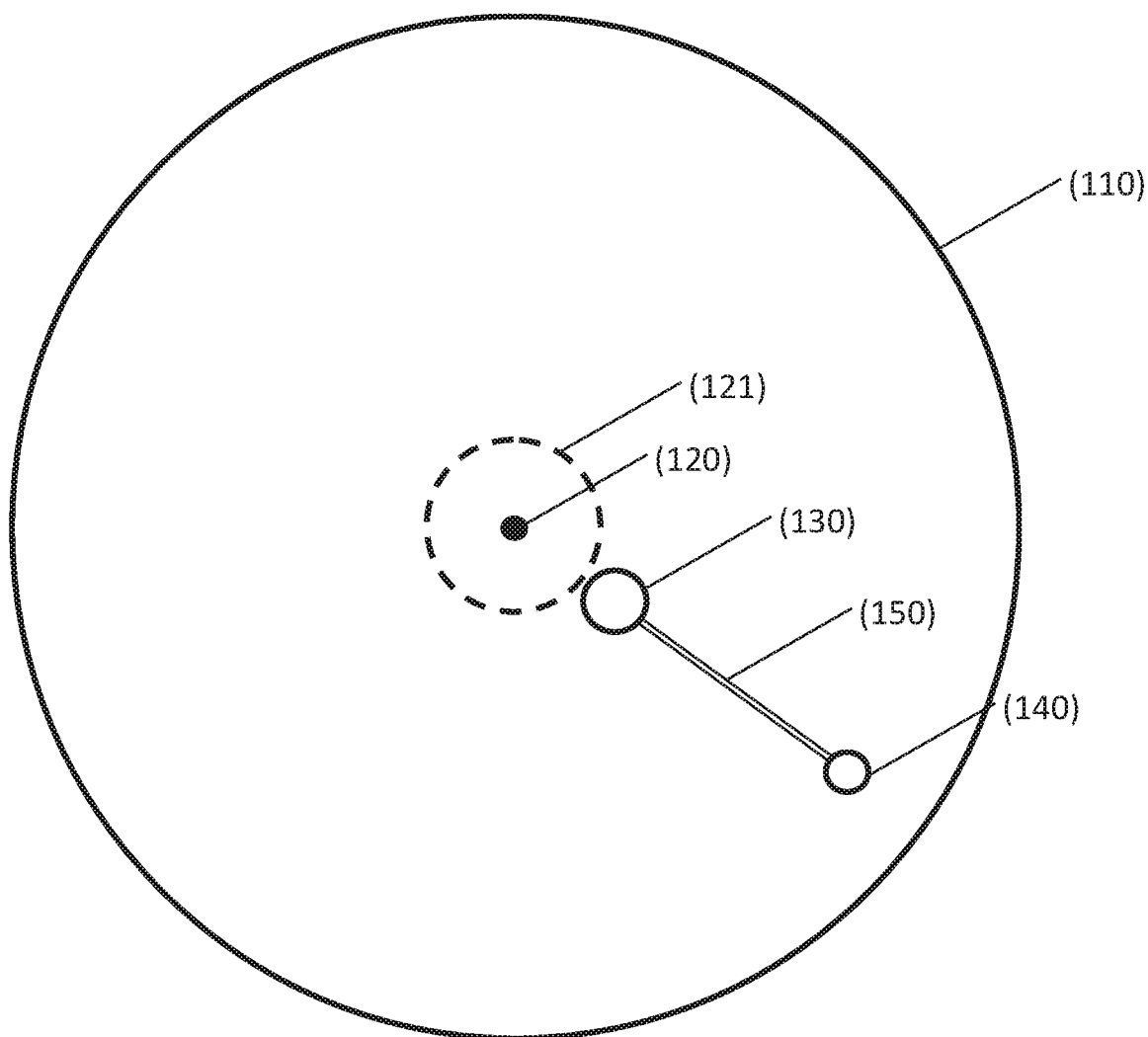
FIG. 1 schematically shows a carrier plate unit used according to the invention having central axis of rotation (110).

FIG. 1 shows a carrier plate unit (110) used according to the invention in the form of a disk. Carrier plate unit (110) has a central axis of rotation (120) and a central region (121) enclosing it. An access opening (130), which is connected via channel (150) to cultivation chamber (140), is arranged proximally to the central axis of rotation (120).

Figure 2:
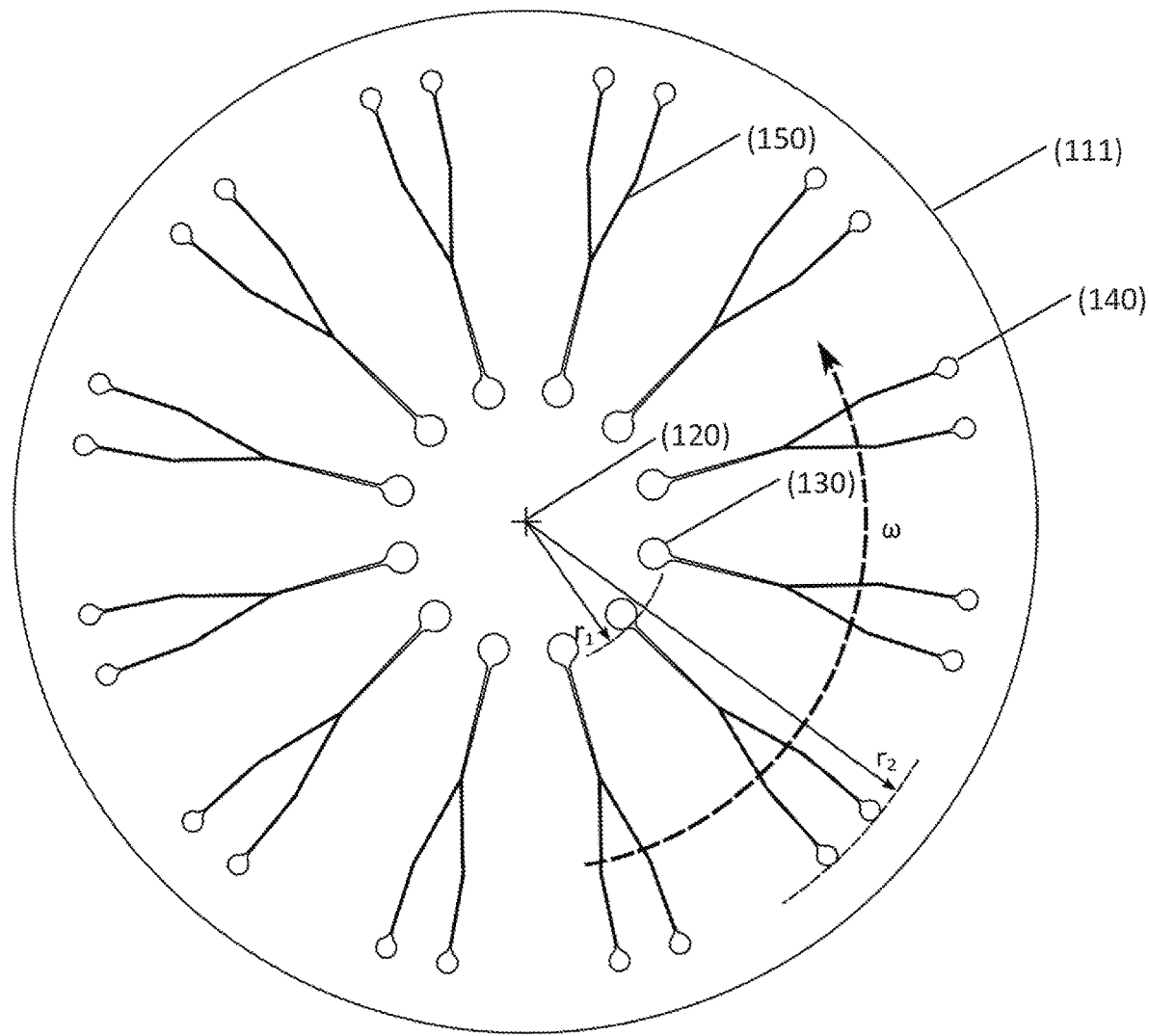
FIG. 2 schematically shows the structure of a first carrier plate (111).

FIG. 2 shows a first carrier plate (111) having central axis of rotation (120) and access openings (130) arranged proximally thereto at distance $r_1$ and cultivation chambers (140) arranged distally at distance $r_2$ to the central axis of rotation (120), wherein the channel (150) connecting the access openings (130) to the cultivation chambers (140) is a branched channel.

Figure 3:
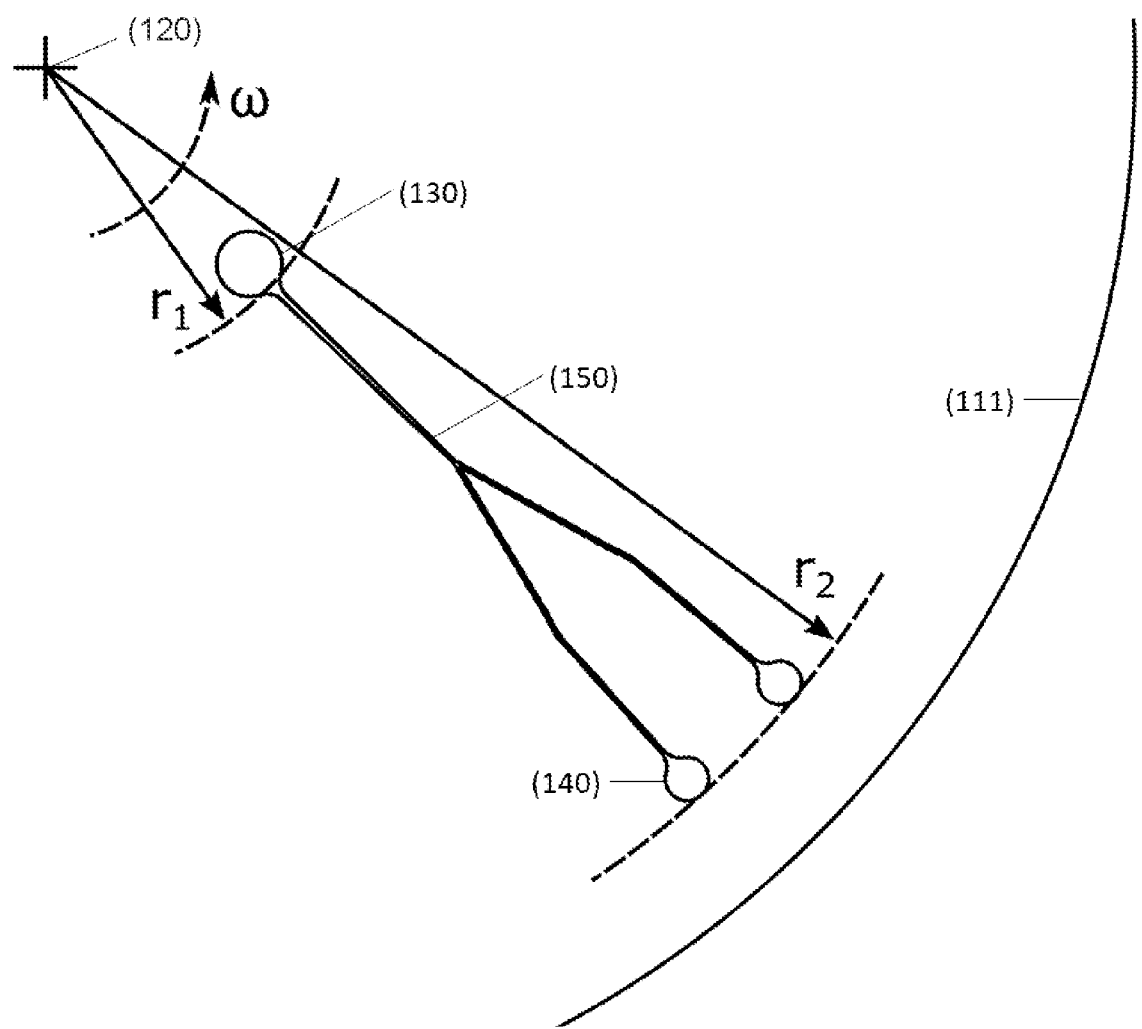
FIG. 3 shows a detail of the first carrier plate (111).

FIG. 3 shows a detail of the central axis of rotation (120) of the first carrier plate (111) and the access opening (130) arranged proximally to the central axis of rotation (120) at distance $r_1$, the cultivation chamber (140) arranged distally at distance $r_2$, and the branched channel (150) connecting the access opening (130) and the cultivation chambers (140). The cultivation chambers (140) are filled with cells by rotation of the carrier plate at angular velocity ω.

Figure 4:
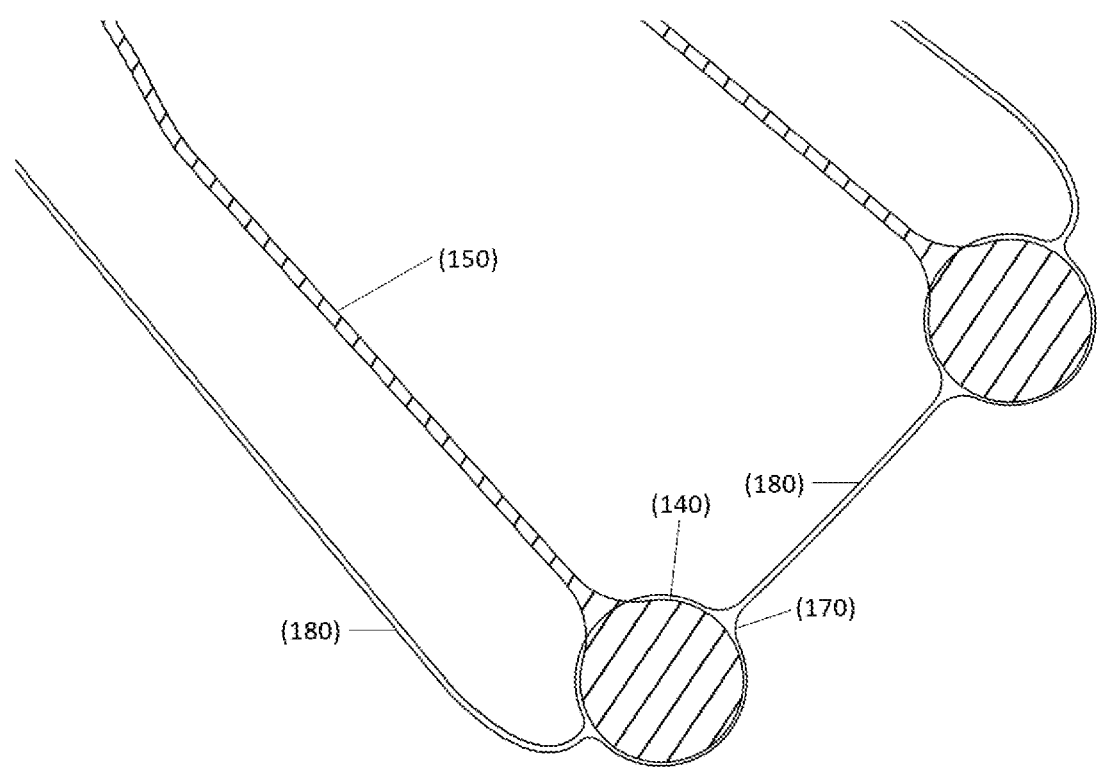
FIG. 4 shows the cultivation chambers (140) of the first carrier plate (111) and media chambers (170) of the second carrier plate (112), which are arranged overlapping.

FIG. 4 shows two cultivation chambers (140) of the first carrier plate, which are arranged overlapping with two media chambers (170) of the second carrier plate and are separated by a membrane. Channel (150) connects access openings (not shown) to the cultivation chambers (140) of the first carrier plate and the media channel (180) connects the media openings (not shown) to a first media chamber (170) and a second media chamber (170) of the second carrier plate. The cultivation chambers (140) and channels (150) of the first carrier plate are shown by dashes.

Figure 5:
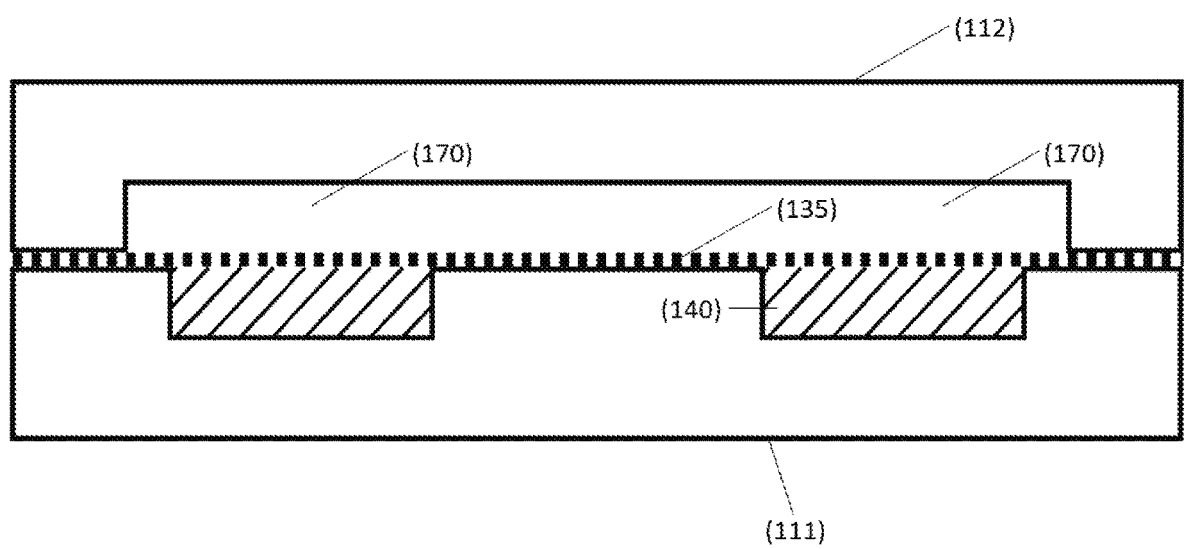
FIG. 5 shows a cross section through the device according to the invention.

FIG. 5 shows a cross section of a carrier plate unit (110) used according to the invention, consisting of a first carrier plate (111) and a second carrier plate (112), which is arranged above the first carrier plate (111). A separating device, in particular membrane (135), is arranged between the first carrier plate (111) and the second carrier plate (112). It separates the cultivation chambers (140) of the first carrier plate (111) from the media chambers (170) of the second carrier plate (112).

FIG. 6 shows the schematic structure of a first carrier plate (111) having access openings (130), which are connected to one or more cultivation chambers (140) via channel (150), and through openings (125) for connecting the device to an external rotational device.

Figure 7:
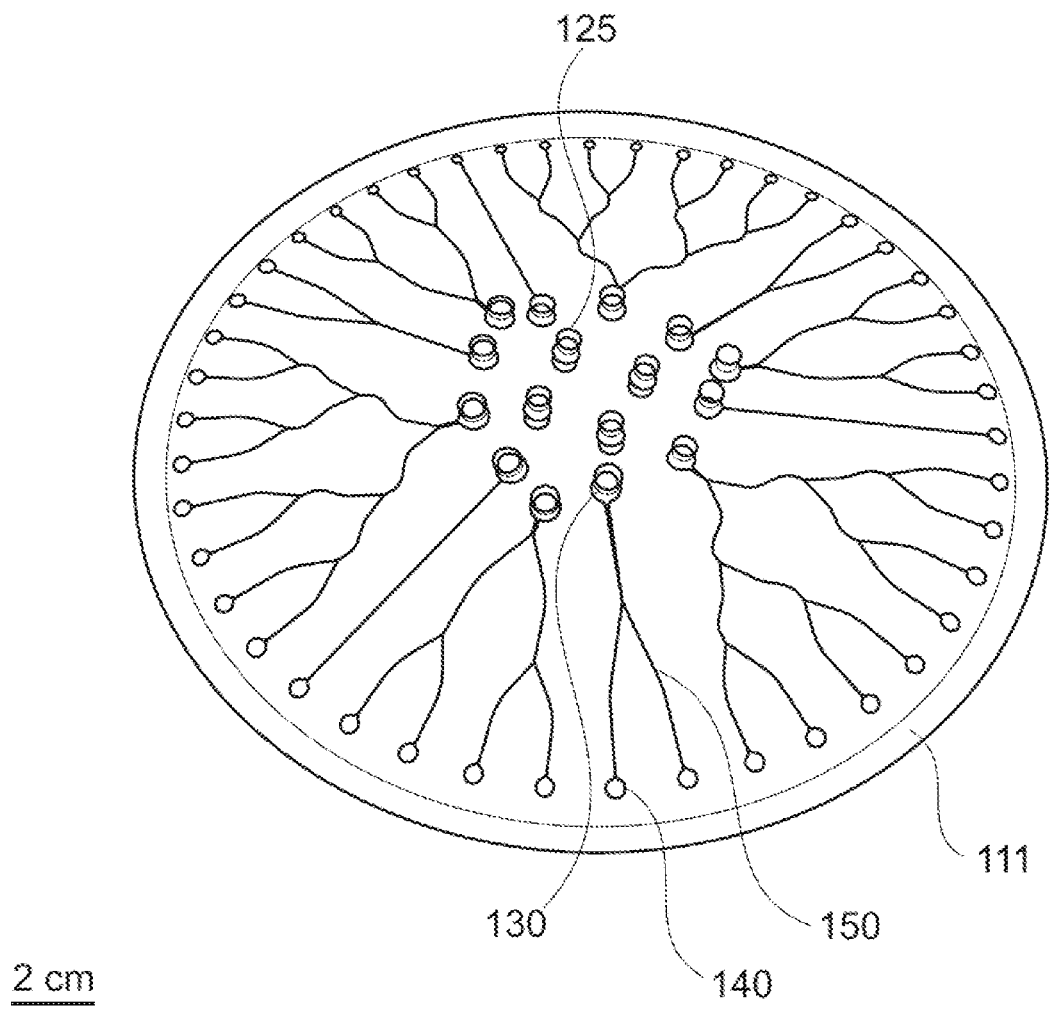
FIG. 7 shows a first carrier plate (111) having colored cultivation chambers (140) and channels (150).

FIG. 7 shows the structure of a first carrier plate (111), wherein the access openings (130), the channels (150), and the cultivation chambers (140) are colored with ink for highlighting. The through openings (125) are not colored. The carrier plate is sealed using an unstructured PDMS layer.

Figure 8:
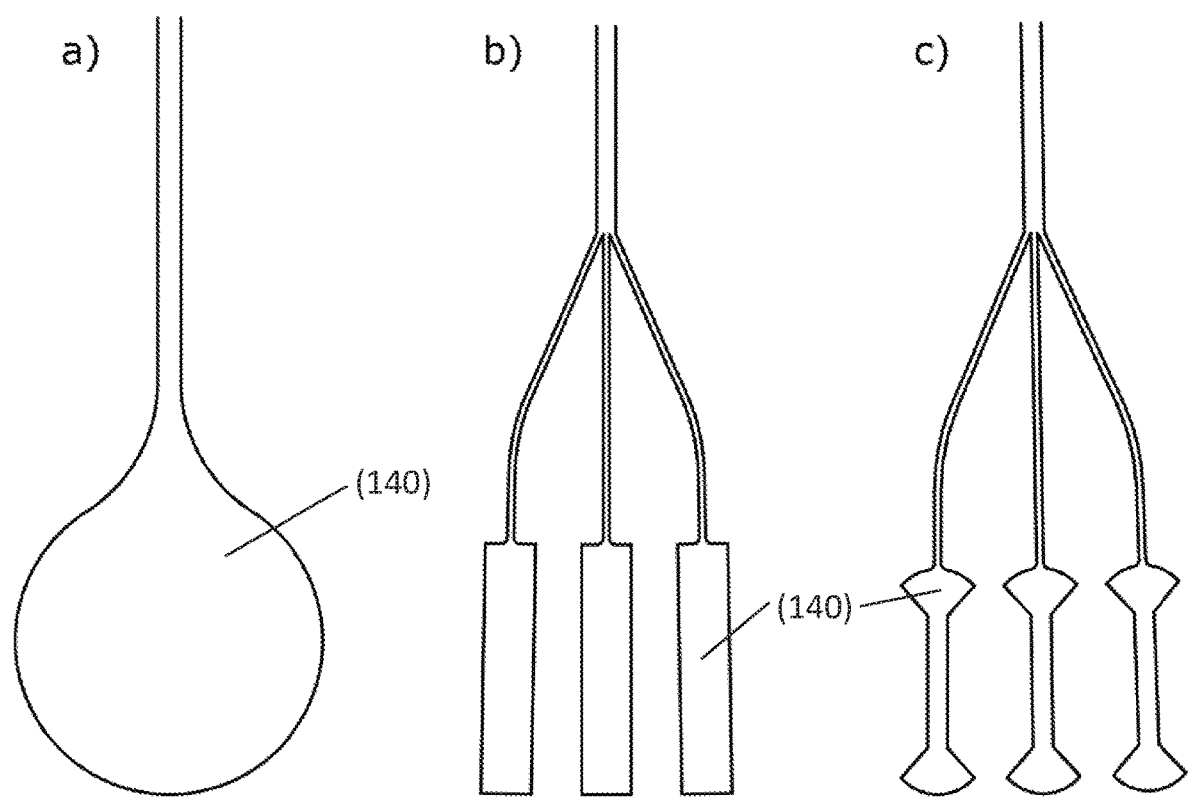
FIG. 8 shows possible cultivation chamber geometries a) round, b) rectangular, and c) dumbbell-shaped.

FIG. 8 shows a schematic illustration of possible cultivation chamber geometries. a) shows a single round cultivation chamber (140), b) shows three rectangular cultivation chambers (140), and c) shows three dumbbell-shaped cultivation chambers (140), which are especially designed for cardiomyocytes.

Figure 9:
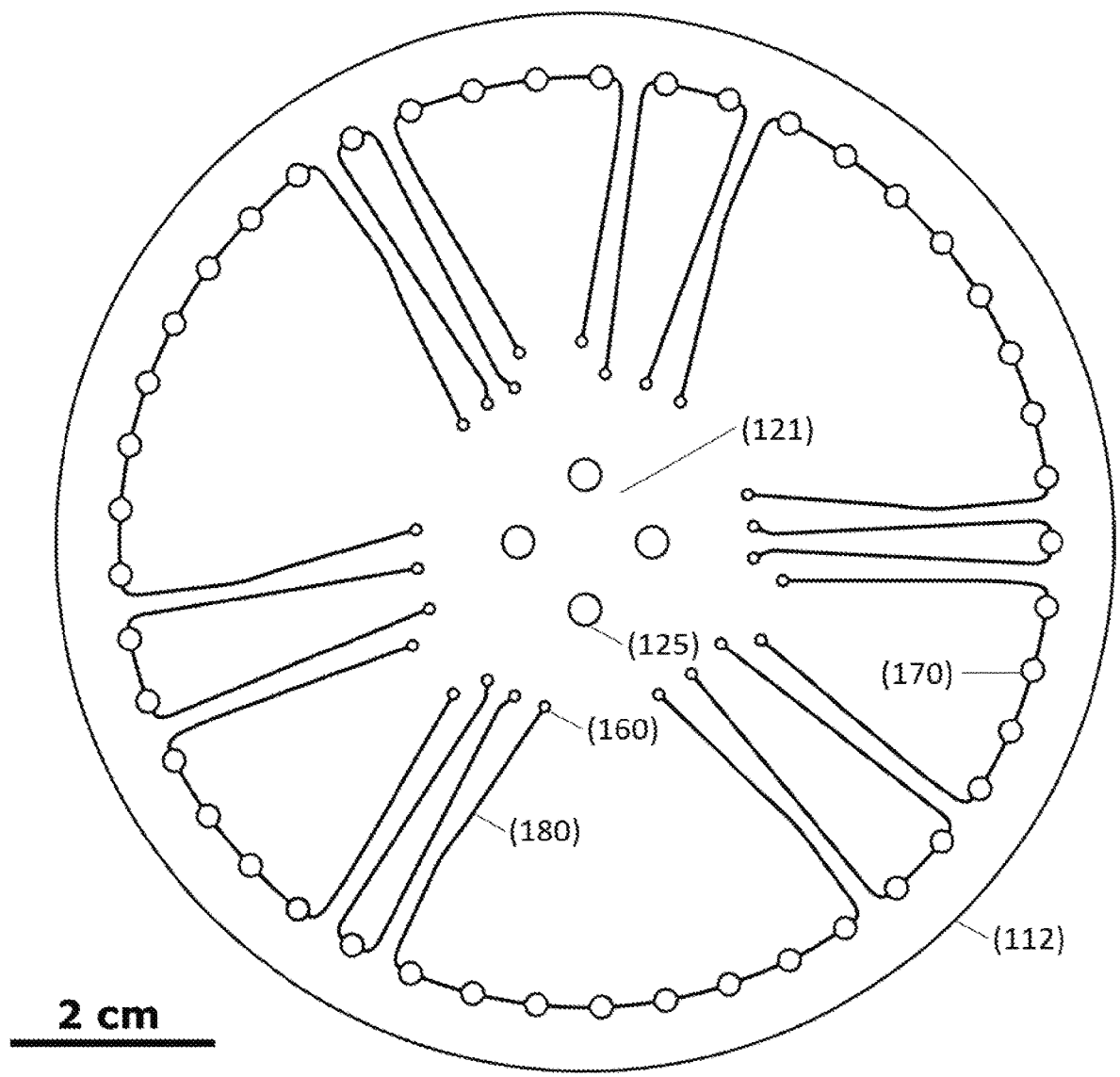
FIG. 9 schematically shows the structure of a second carrier plate (112).

FIG. 9 shows a schematic illustration of the second carrier plate (112) having connecting devices arranged in the central region (121), in particular through openings (125), media openings (160), media chambers (170), and the channels (180) connecting the media inlets (160) to the media chambers (170). In this case, each two media openings (160) are connected to one media chamber (170) or multiple media chambers (170), which are then connected in series.

FIG. 10 shows the schematic structure of the separating device (135), which is arranged between the first carrier plate (111) and the second carrier plate. The black dots represent permeable pores, which are arranged in a hexagonal grid. The differing density of the pores represents regions of differing porosity of the separating device (135), in particular the membrane.

Figure 11:
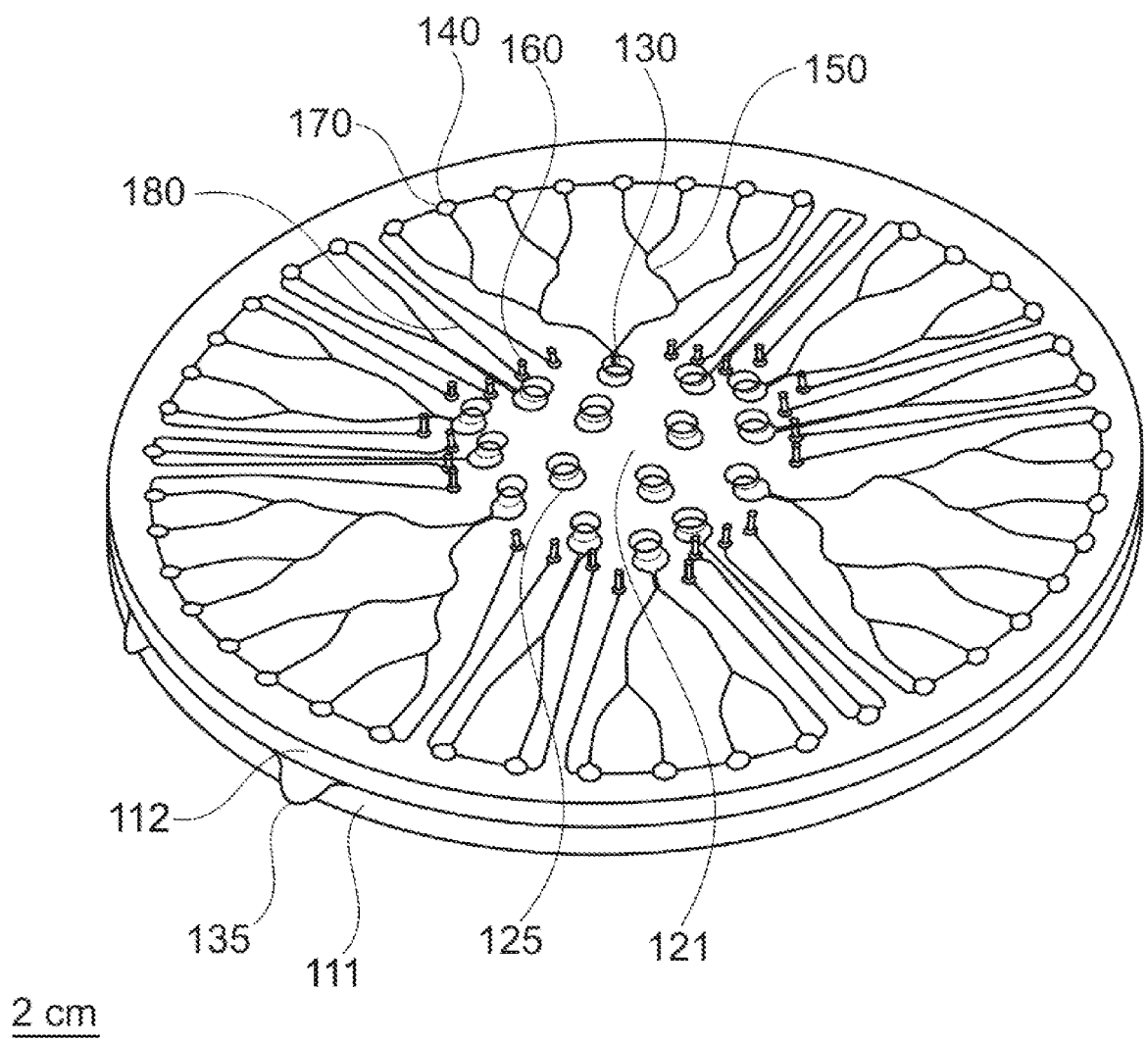

FIG. 11 shows the device used according to the invention consisting of a first carrier plate (111), a membrane (135), and a second carrier plate (112). In the central region (121), the device has four connecting devices, in particular through openings (125) for fastening the device on an external motor. The larger access openings (130) and the smaller media openings (160) can be seen proximally thereto, and also channels (150) of the first carrier plate (111) and media channels (180) of the second carrier plate (112) and the cultivation chambers (140) and media chambers (170), which are arranged overlapping.

Figure 12:
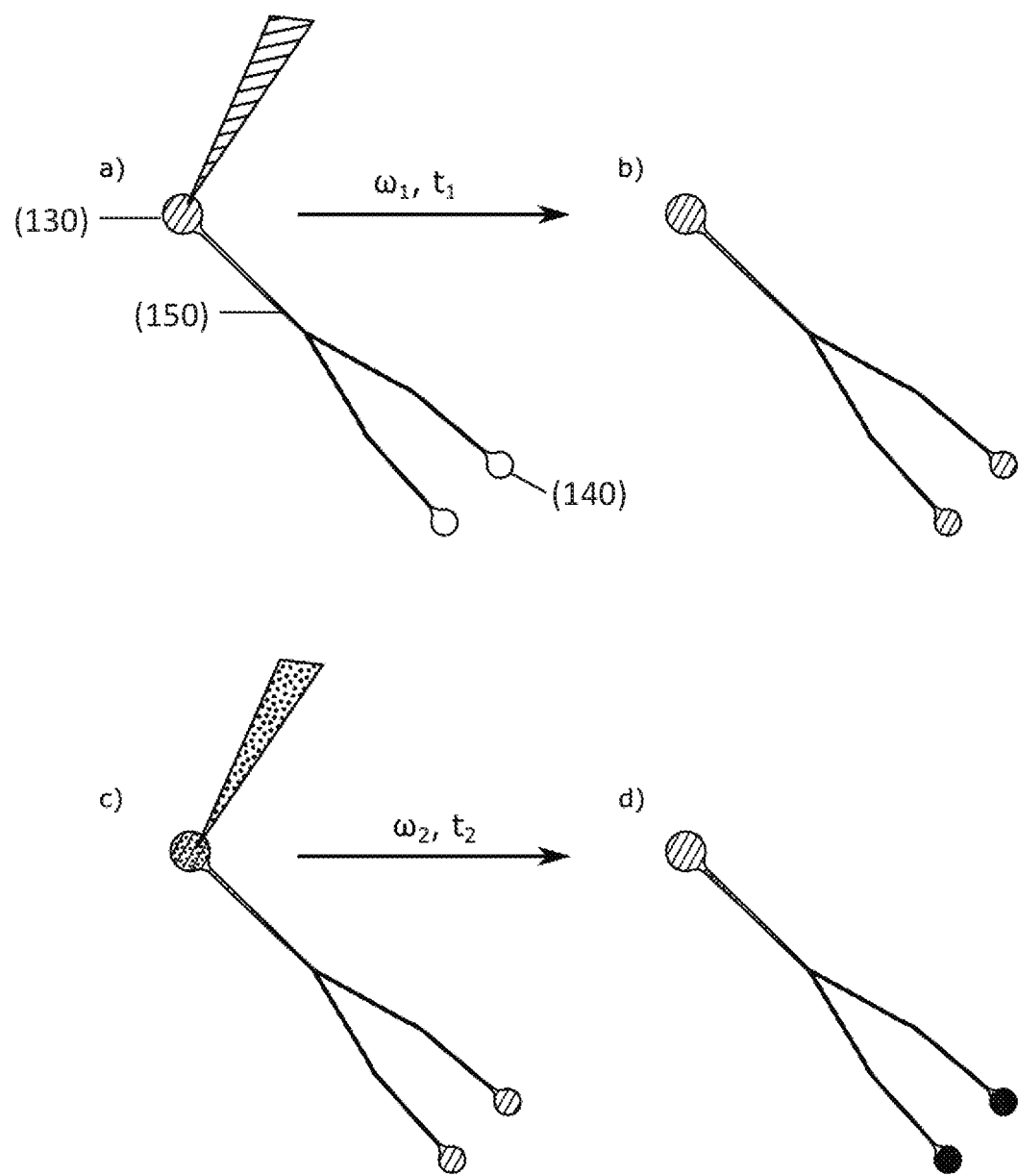
FIG. 12 shows the required steps for filling the cultivation chambers (140).

FIG. 12 shows the steps required for charging the cultivation chambers (140): a) pipetting cell medium into access opening (130), b) rotating ($\omega_1$) the device for $t_1$ so that all channels (150) and cultivation chambers (140) are filled with medium and air bubbles are removed, c) pipetting the cell suspension into access opening (130), and d) further rotation ($\omega_2$) for $t_2$, so that all cells are conveyed into the cultivation chambers (140) and are preferably provided in greater density therein.

Figure 13:
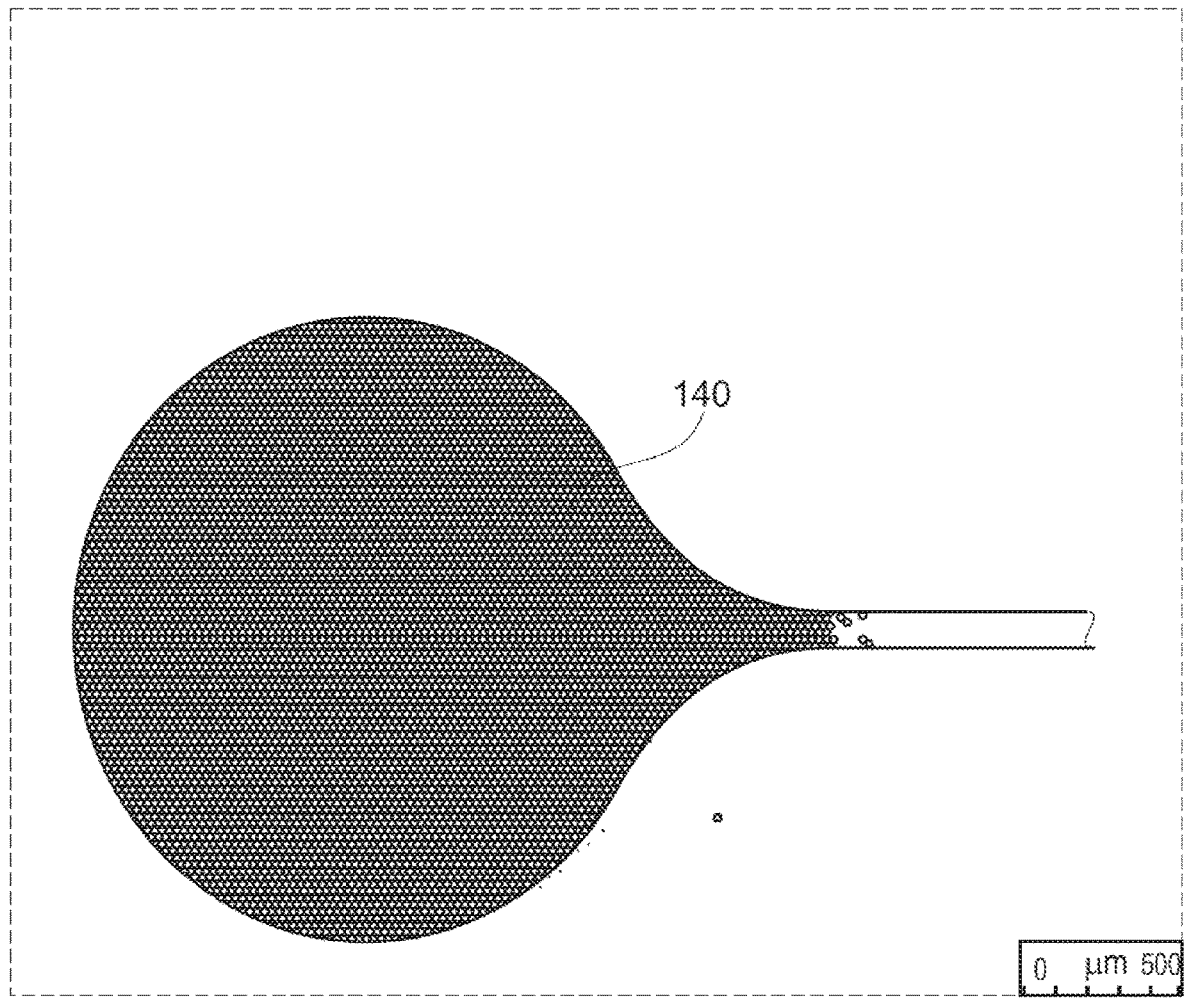
FIG. 13 shows a round cultivation chamber (140) filled with cells.

FIG. 13 shows a round cultivation chamber (140) of the first carrier plate (111) filled with cells (fibroblasts). The cells were conveyed by rotation of the carrier plate into the cultivation chamber (140) and accumulated therein.

Figure 14:
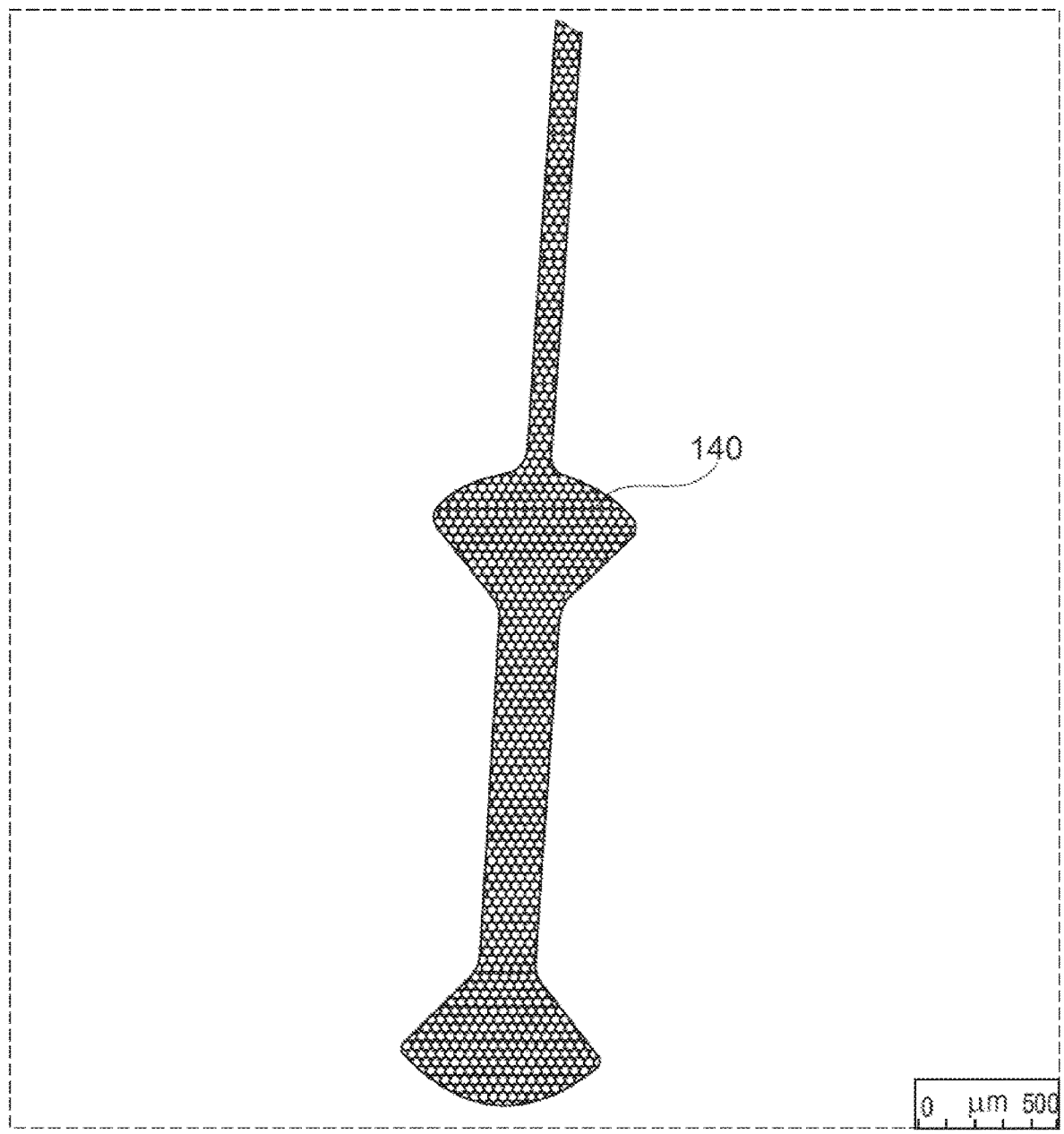
FIG. 14 shows a dumbbell-shaped cultivation chamber (140) filled with cells.

FIG. 14 shows a dumbbell-shaped cultivation chamber (140) of the first carrier plate filled with cells (cardiomyocytes).

Figure 15:
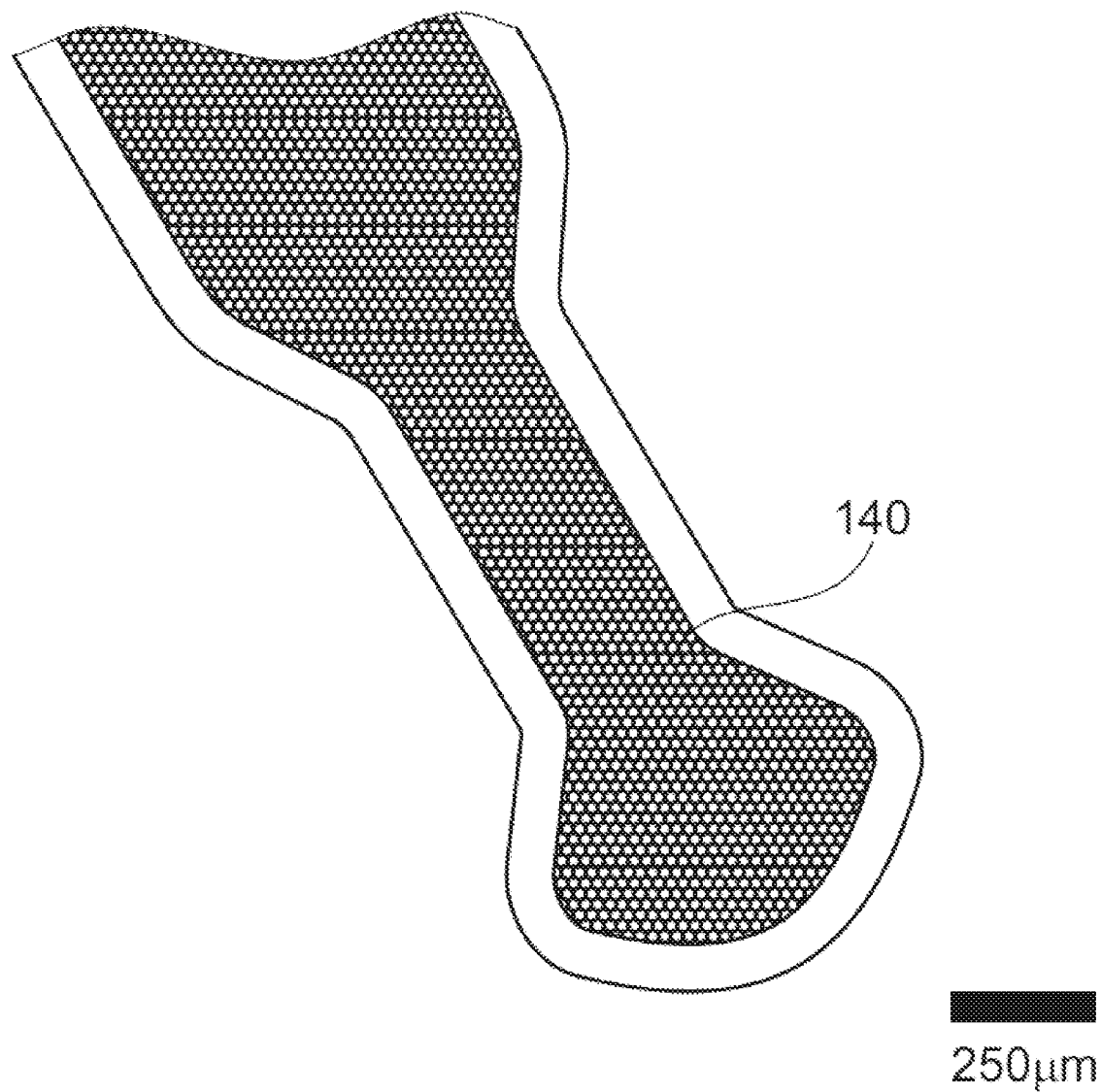
FIG. 15 shows a laser-cut cultivation chamber (140) filled with cells.

FIG. 15 shows a laser-cut cultivation chamber (140) of the first carrier plate filled with cells (fibroblasts).

Figure 16:
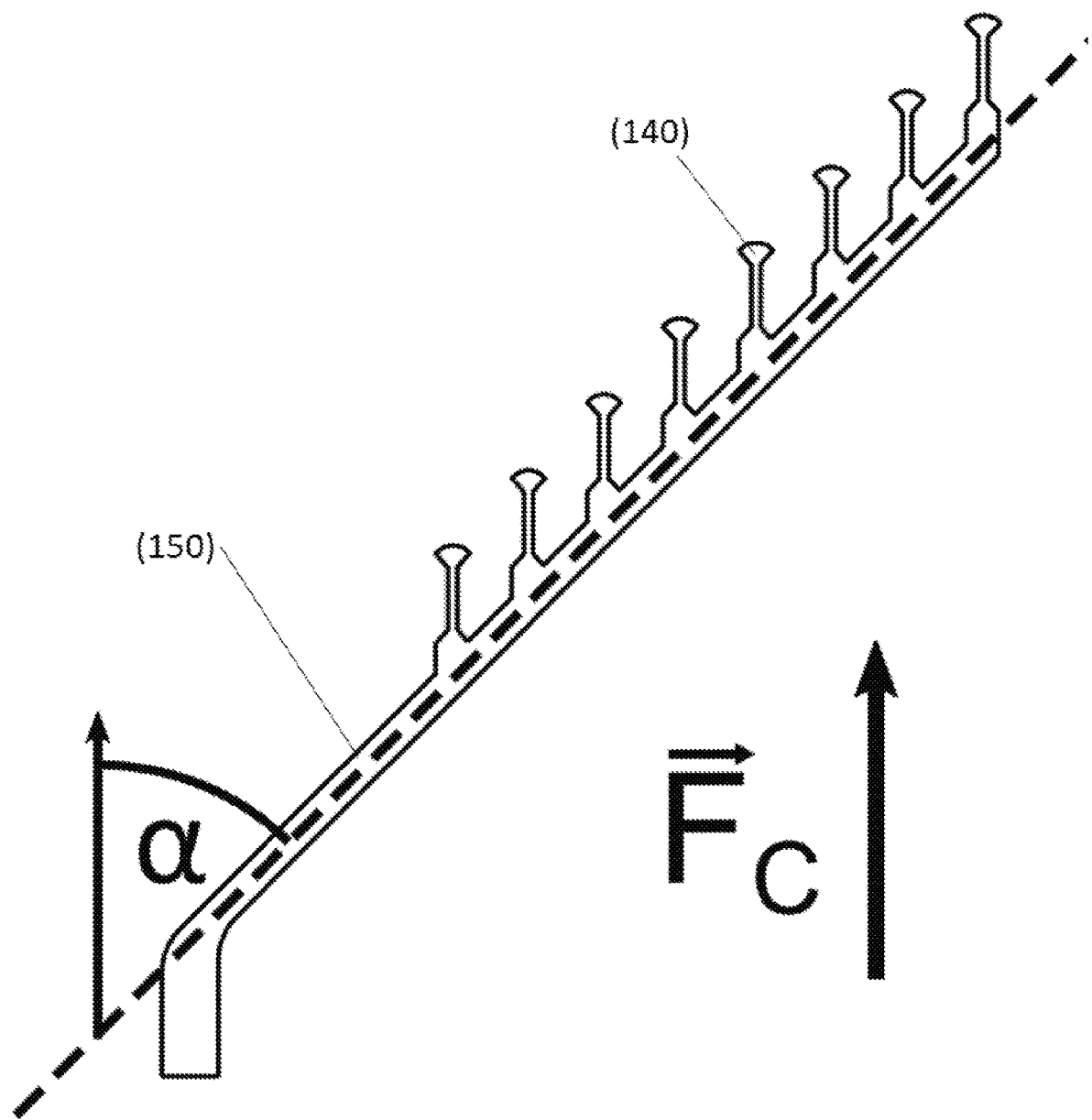
FIG. 16 shows a channel (150) inclined by the angle α having cultivation chambers (140).

FIG. 16 shows cultivation chambers (140) arranged along a channel (150). In this case, the channel (150) is inclined by a defined angle α in relation to the direction of the centrifugal force $F_C$ generated by rotation.

Figure 17:
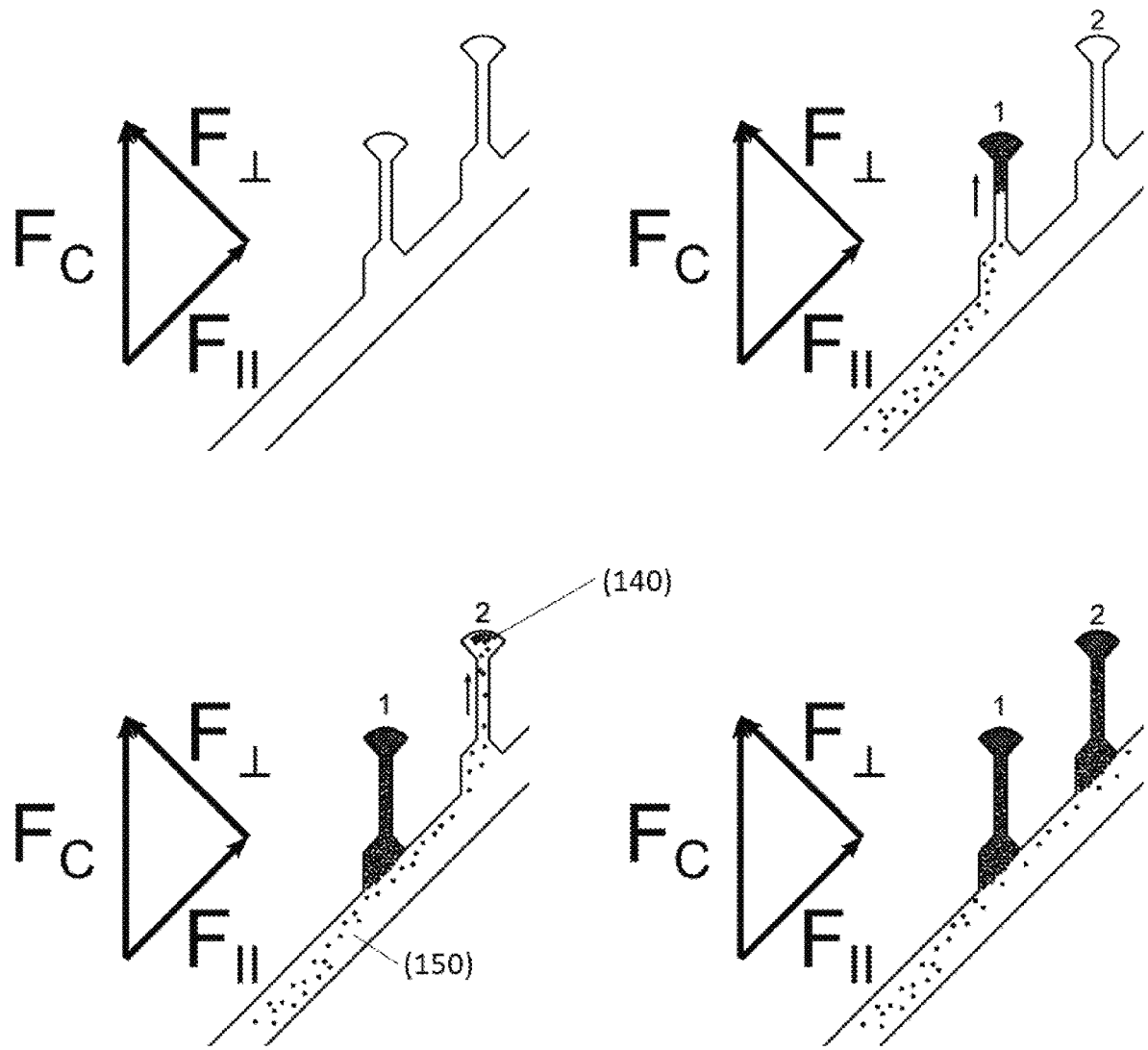
FIG. 17 schematically shows the filling of the cultivation chambers effectuated by rotation.

FIG. 17 schematically shows the filling of the cultivation chambers (140) by the centrifugal force $F_C$, which may be split into the down force $F_{II}$ along the channel (150) inclined by the angle α and the contact pressure force $F_\perp$, which acts perpendicularly on the peripherally located channel wall of the channel (150) inclined by the angle α.

FIG. 18 shows three-dimensional cell complexes (cardiomyocytes) obtained by means of the method according to the invention in eight cultivation chambers (140) of the device arranged along a channel (150).

Figure 19:
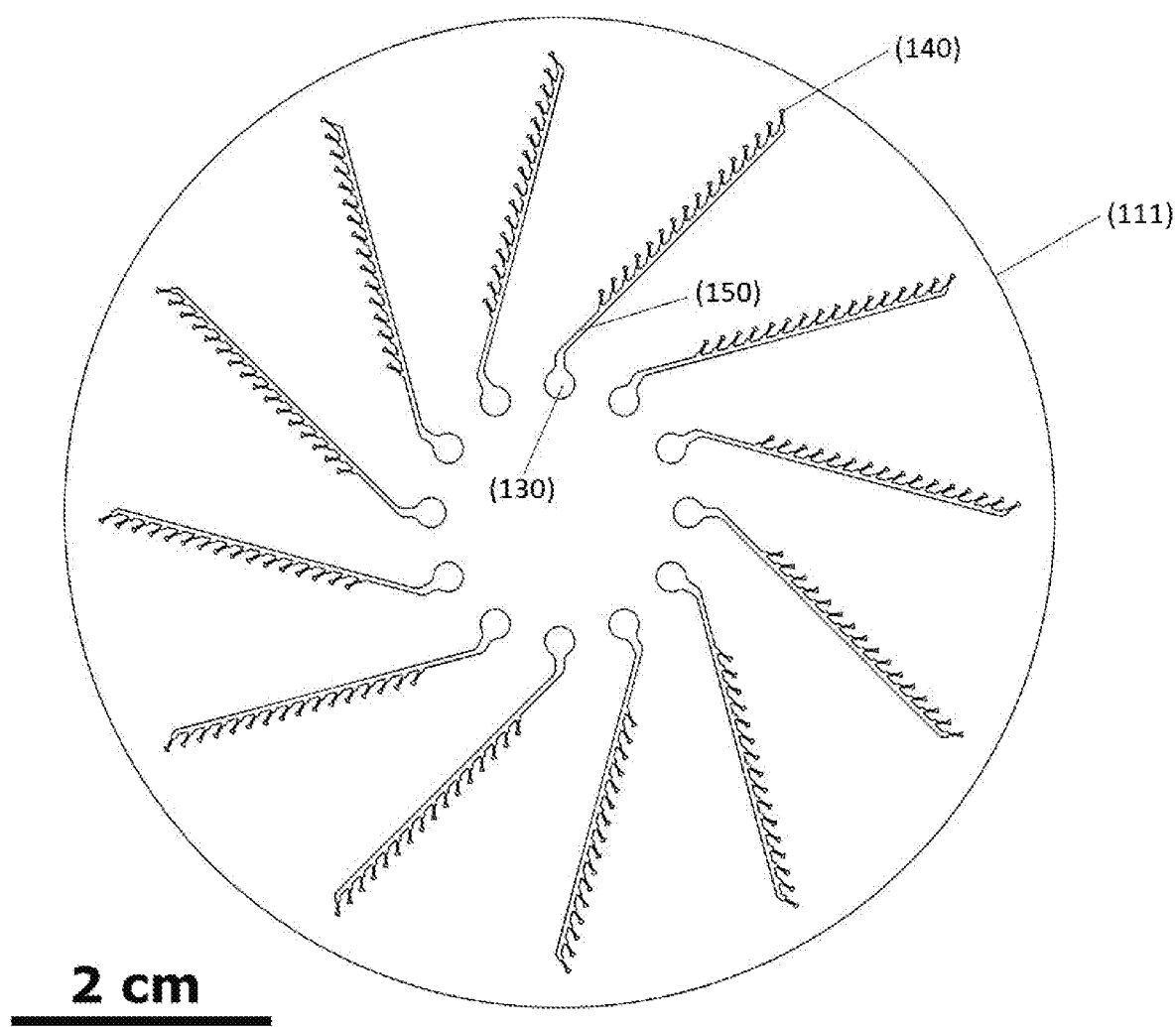
FIG. 19 schematically shows a possible structure of a first carrier plate (111) used according to the invention having central axis of rotation.

FIG. 19 shows an embodiment of the device used according to the invention, in which, on a first carrier plate (111), multiple access openings (130) arranged around a central axis of rotation are each connected via an inclined channel (150) to cultivation chambers (140) arranged along the channel (150).

Figure 20:
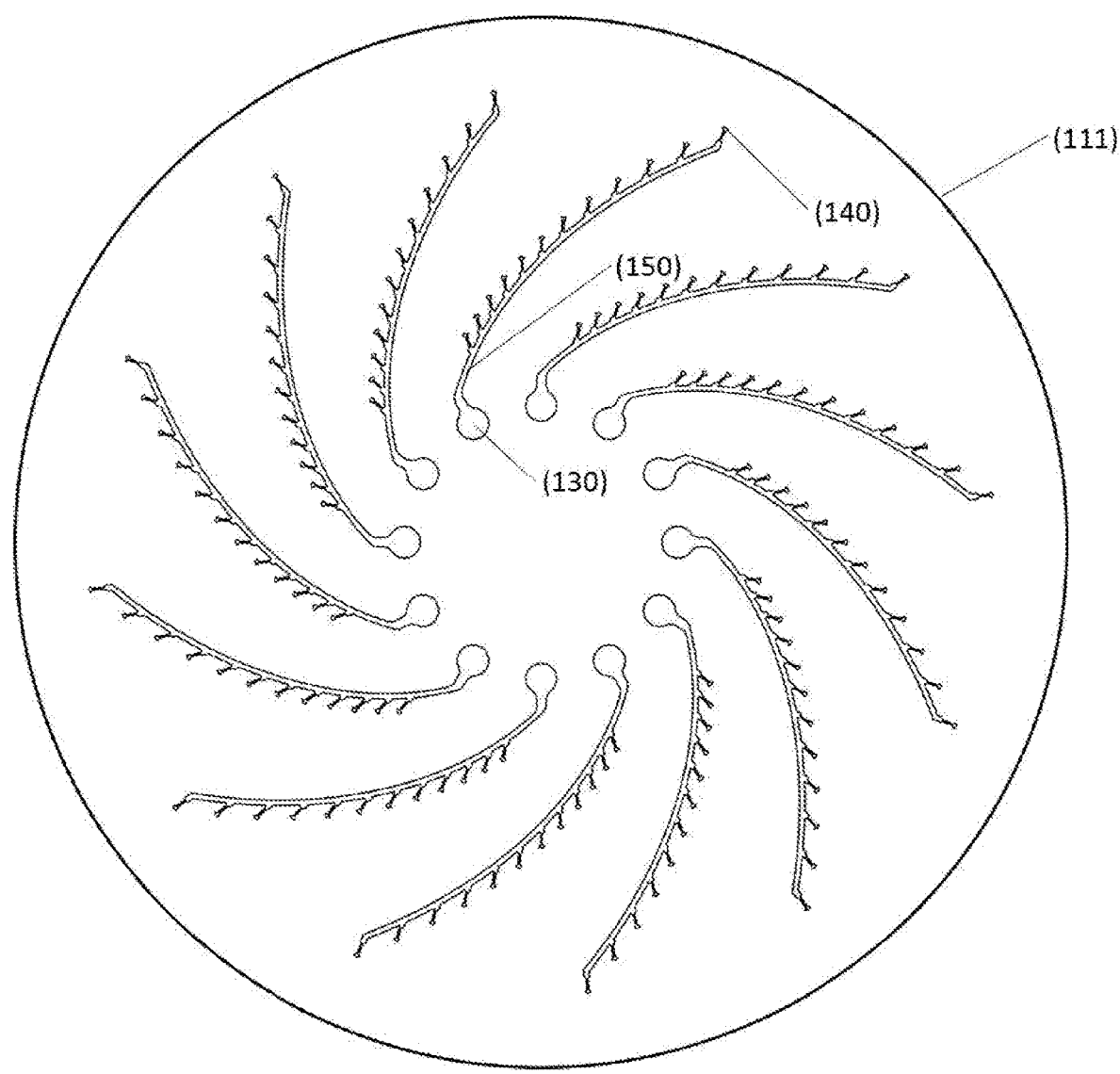
FIG. 20 schematically shows a further possible structure of a first carrier plate (111) used according to the invention having central axis of rotation.

FIG. 20 shows an embodiment of the device used according to the invention, in which, on a first carrier plate (111), multiple access openings (130) arranged around a central axis of rotation are each connected via a curved channel (150) to cultivation chambers (140) arranged along the channel (150). The cells are conveyed into the cultivation chambers (140) by the centrifugal force Fc.

Figure 21:
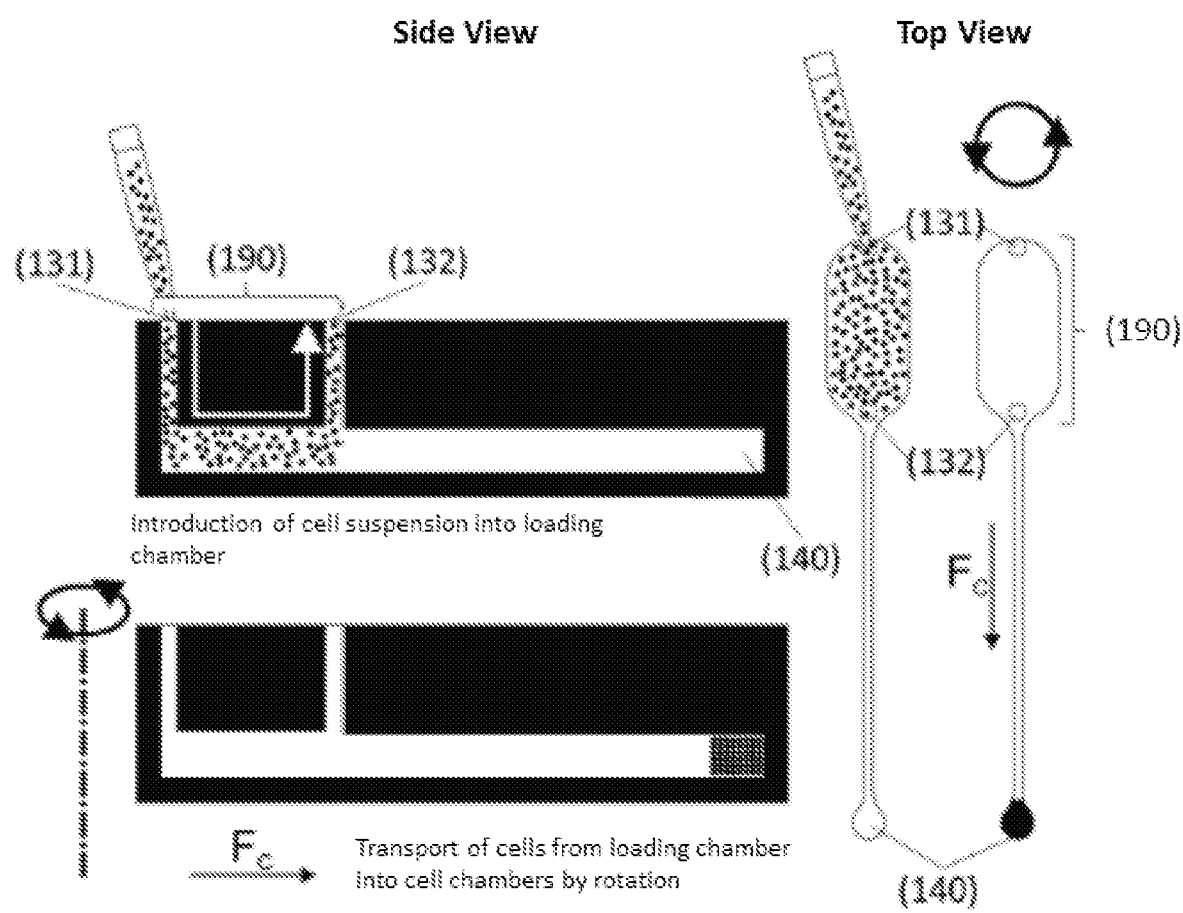
FIG. 21 schematically shows an embodiment of a device used according to the invention, in which the access opening (130) is formed as a loading chamber (190).

FIG. 21 shows an embodiment of the device according to the invention, in which the at least one access opening (130) is designed as a loading chamber (190), which comprises two access openings (131, 132).

Figure 22:
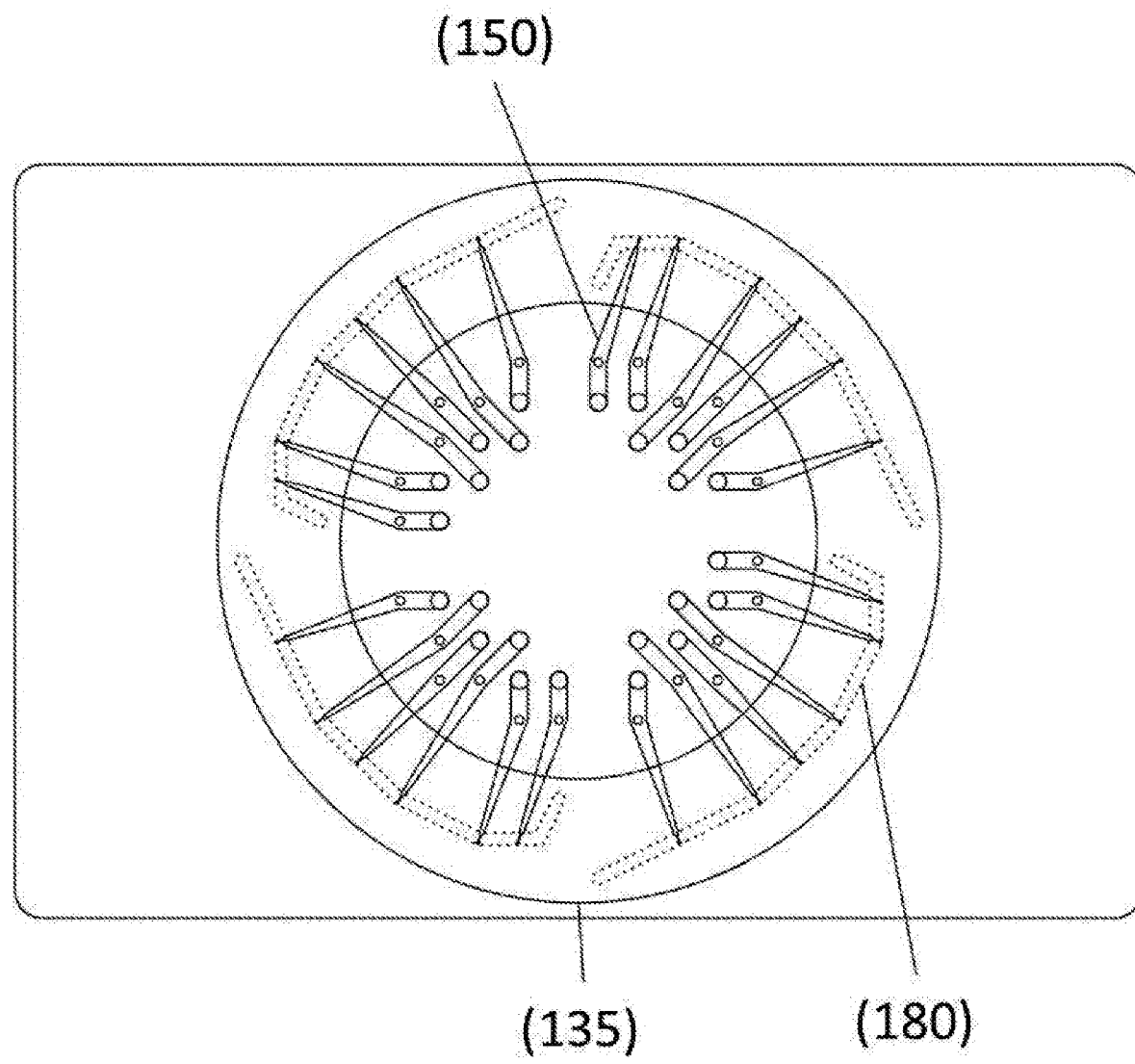
FIG. 22 schematically shows a device used according to the invention having central axis of rotation in microtitration format.

FIG. 22 shows an embodiment in which the device comprising a central axis of rotation is designed for the cultivation of cells in the micro-titration plate format. The channels (150), the media channels (180), and the membrane (135) are shown.

Figure 23:
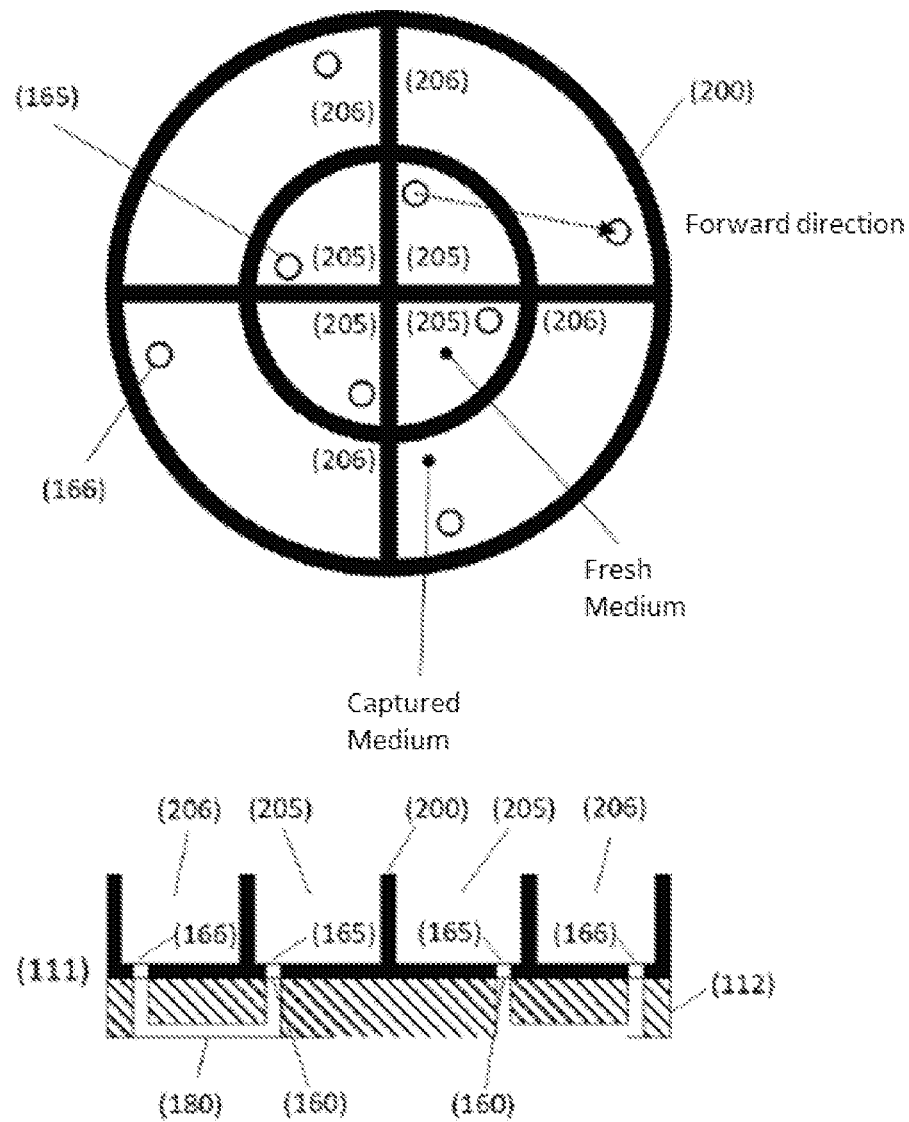
FIG. 23 shows the structure of a reservoir (200) for cell culture medium or active ingredients to be studied of a device used according to the invention having central axis of rotation.

FIG. 23 shows an embodiment of the device used according to the invention, in which the carrier plate unit (110) additionally comprises a reservoir (200) for liquids, in particular for cell culture medium or active ingredients to be studied, which is arranged above a second carrier plate (112) and comprises separate containers (205), which are arranged proximally to the centrally located axis of rotation of the carrier plate unit, having media outlets (165) and separate containers (206), which are arranged distally to the centrally located axis of rotation of the carrier plate, unit having media inlets (166), wherein the media outlets (165) each have a fluid connection via media openings (160) and media channels (180) of the second carrier plate (112) located underneath to the media inlets (166).

Figure 24:
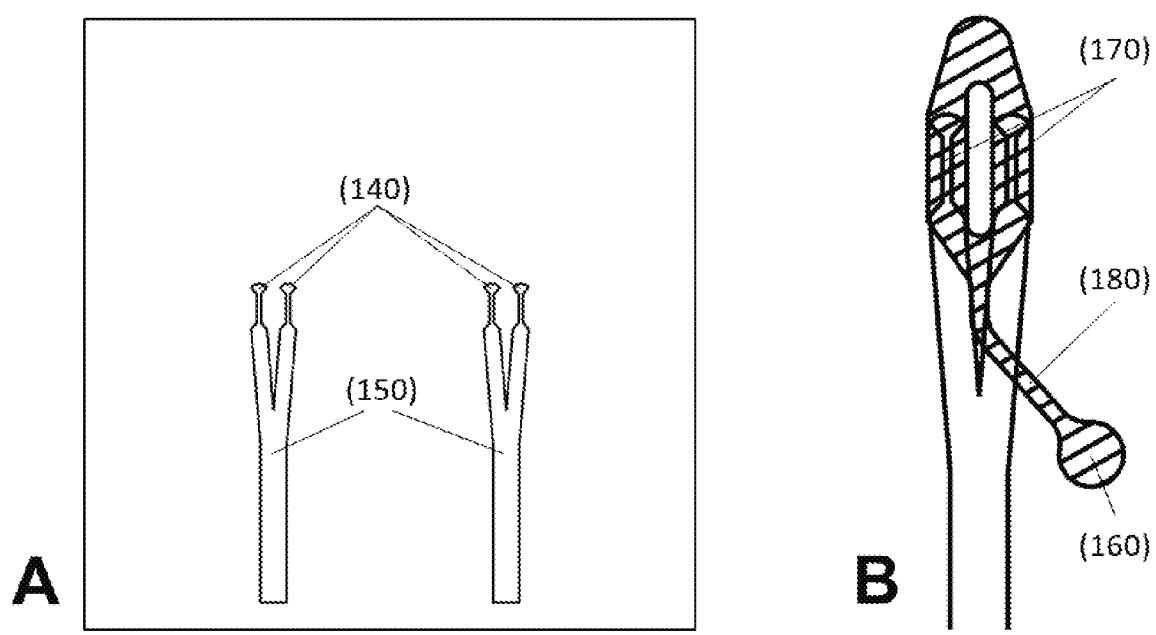
FIG. 24 shows, in A, the structure of a device used according to the invention and, in B, a media supply of the cultivation chambers.

FIG. 24 shows, in A, the structure of a device used according to the invention without central axis of rotation having respectively two branched channels (150) and cultivation chambers (140), and, in B, a media supply of the cultivation chambers (140) with a media opening (160), media chamber (170), and a channel (180) connecting the media opening (160) to the media chamber (170).

Figure 25:
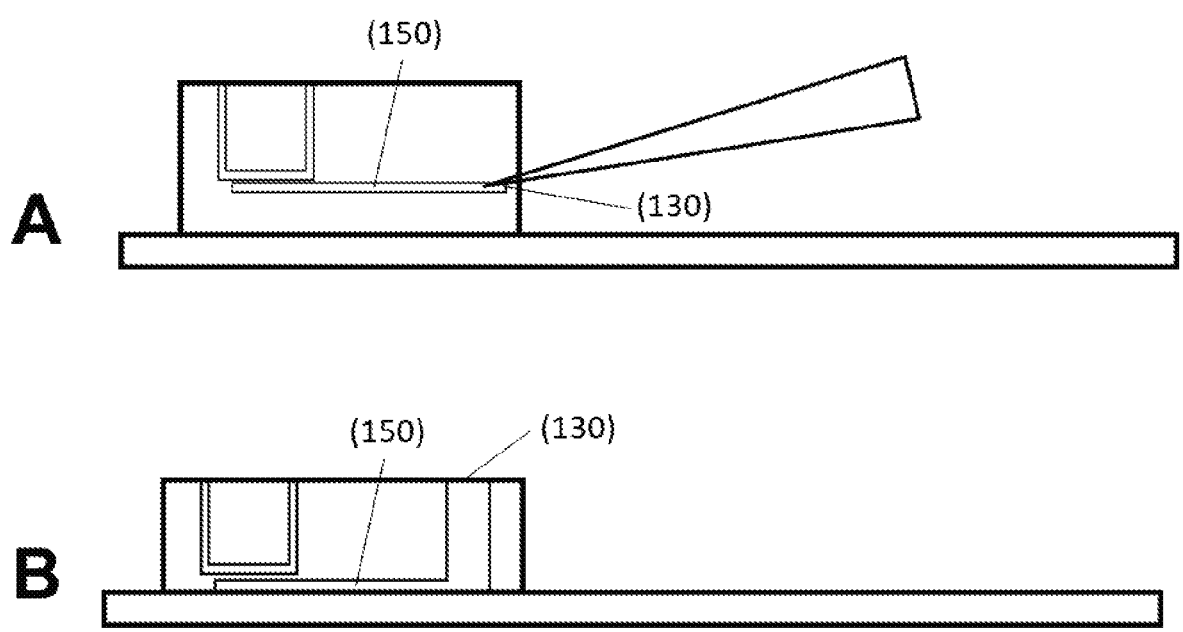
FIG. 25 shows, in A, a device used according to the invention having lateral access opening and, in B, a device used according to the invention in which the base of the channel (150) is formed by a glass plate.

FIG. 25 shows, in A, a device used according to the invention having lateral access opening (130) and, in B, a device used according to the invention in which the base of the channel (150) is formed by a glass plate.

Figure 26:
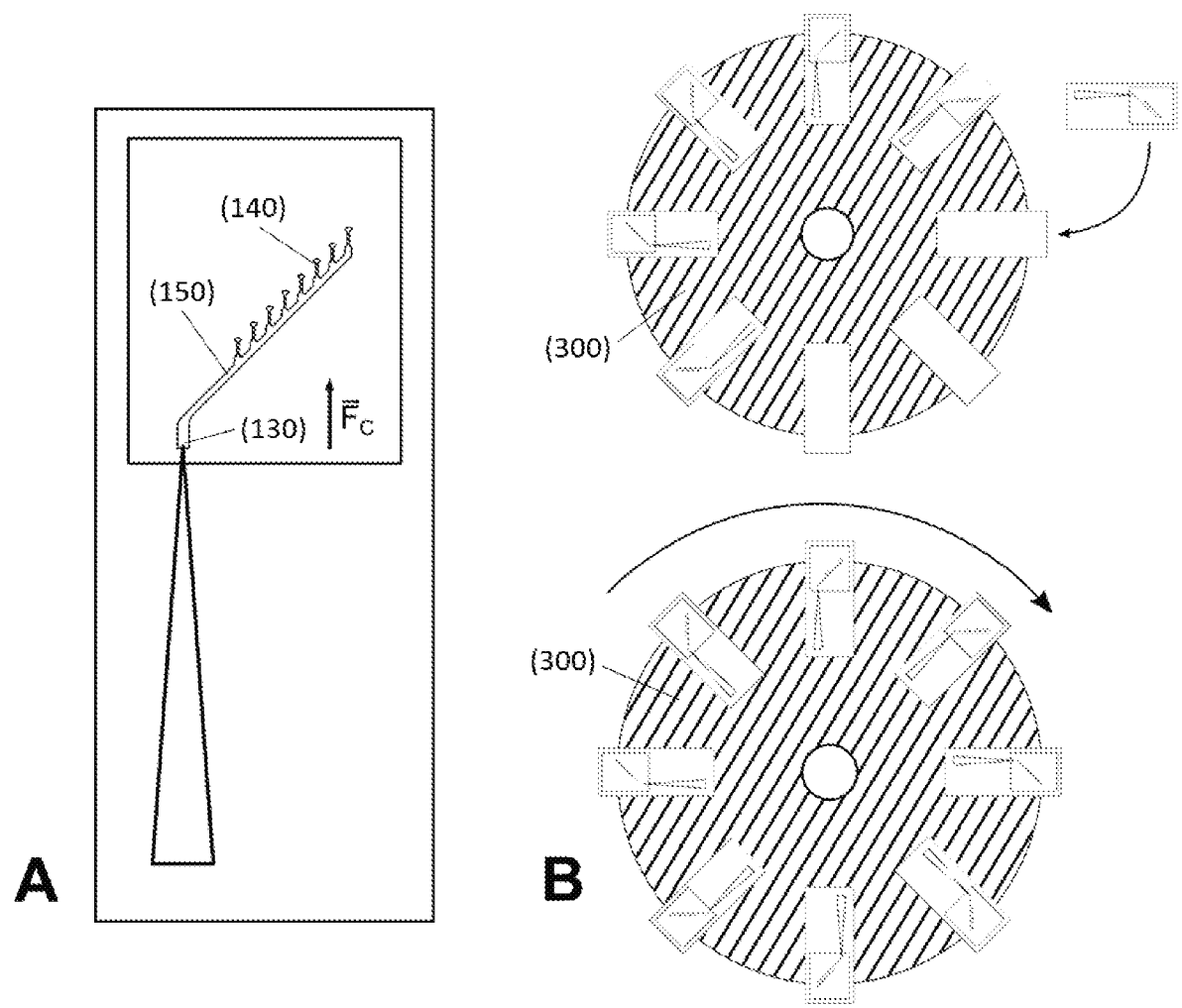
FIG. 26 shows, in A, a device used according to the invention having an inclined channel (150) and cultivation chambers (140). In B, devices used according to the invention are shown before (top) and during (bottom) the rotation around the axis of rotation of the rotational device (300).

FIG. 26 shows, in A, a device used according to the invention having an access opening (130), an inclined channel (150), and cultivation chambers (140) directly adjoining the channel (150). In B, devices used according to the invention are shown before (top) and during (bottom) the rotation around the axis of rotation of the rotational device (300).

Figure 27:
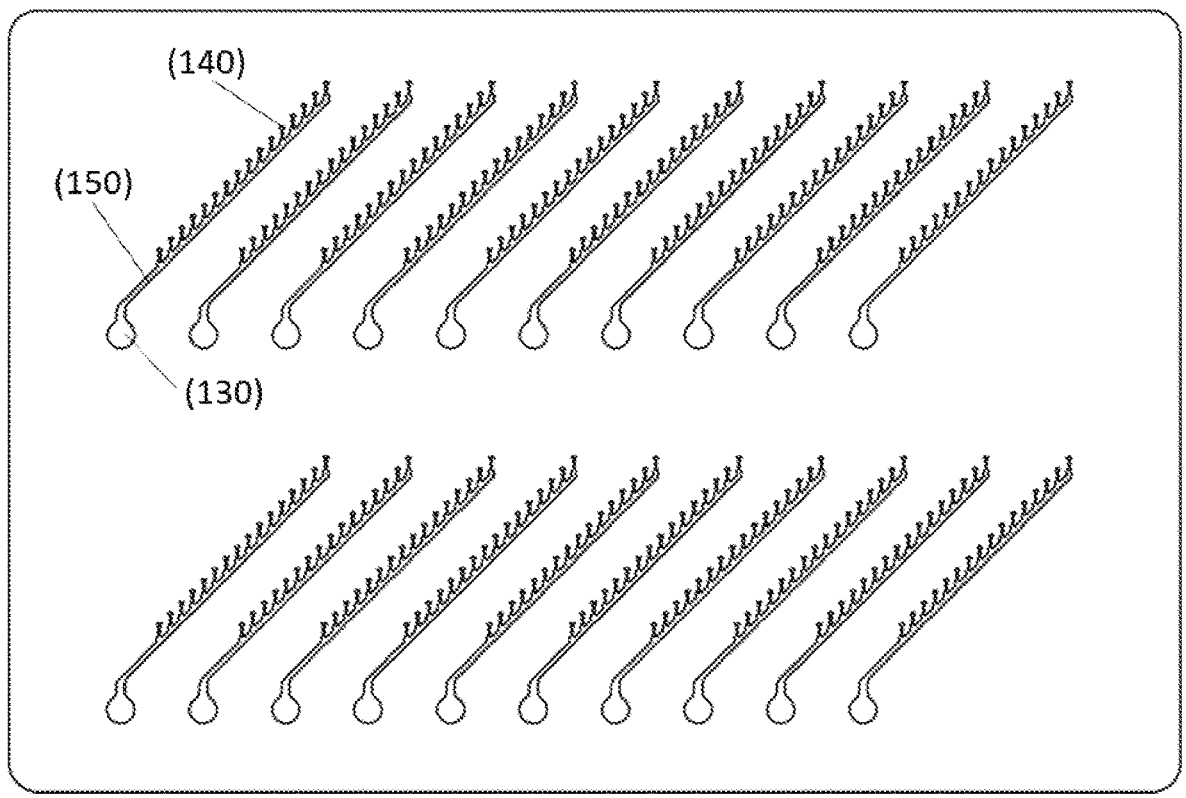
FIG. 27 shows a device used according to the invention without central axis of rotation in microtitration format.

FIG. 27 shows a device used according to the invention without central axis of rotation in the microtitration format having an access opening (130), an inclined channel (150), and cultivation chambers (140) directly adjoining the channel (150).

Figure 28:
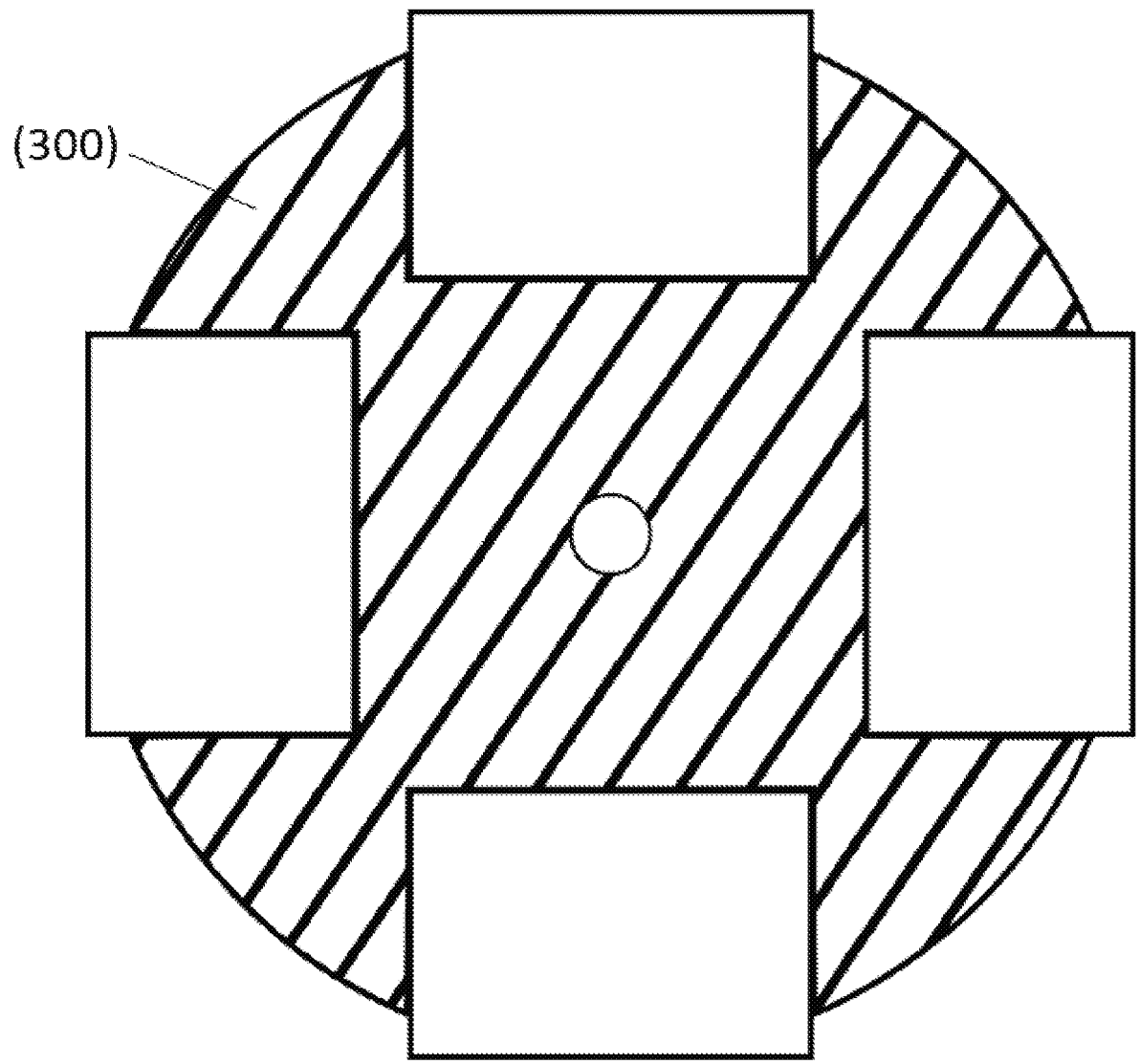
FIG. 28 shows a rotational device (300), in which devices used according to the invention without central axis of rotation in microtitration format can be introduced.

FIG. 28 shows a rotational device (300), in which devices used according to the invention without central axis of rotation in the microtitration format can be introduced.

Figure 29:
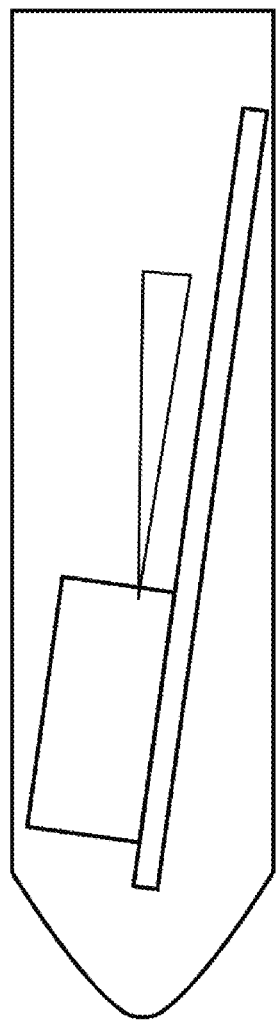
FIG. 29 shows an embodiment in which a device used according to the invention without central axis of rotation has been introduced into a centrifuge tube to carry out the method according to the invention in a conventional laboratory centrifuge.

FIG. 29 shows an embodiment in which a device used according to the invention without central axis of rotation was introduced into a centrifuge tube to carry out the method according to the invention in a conventional laboratory centrifuge.

Figure 30:
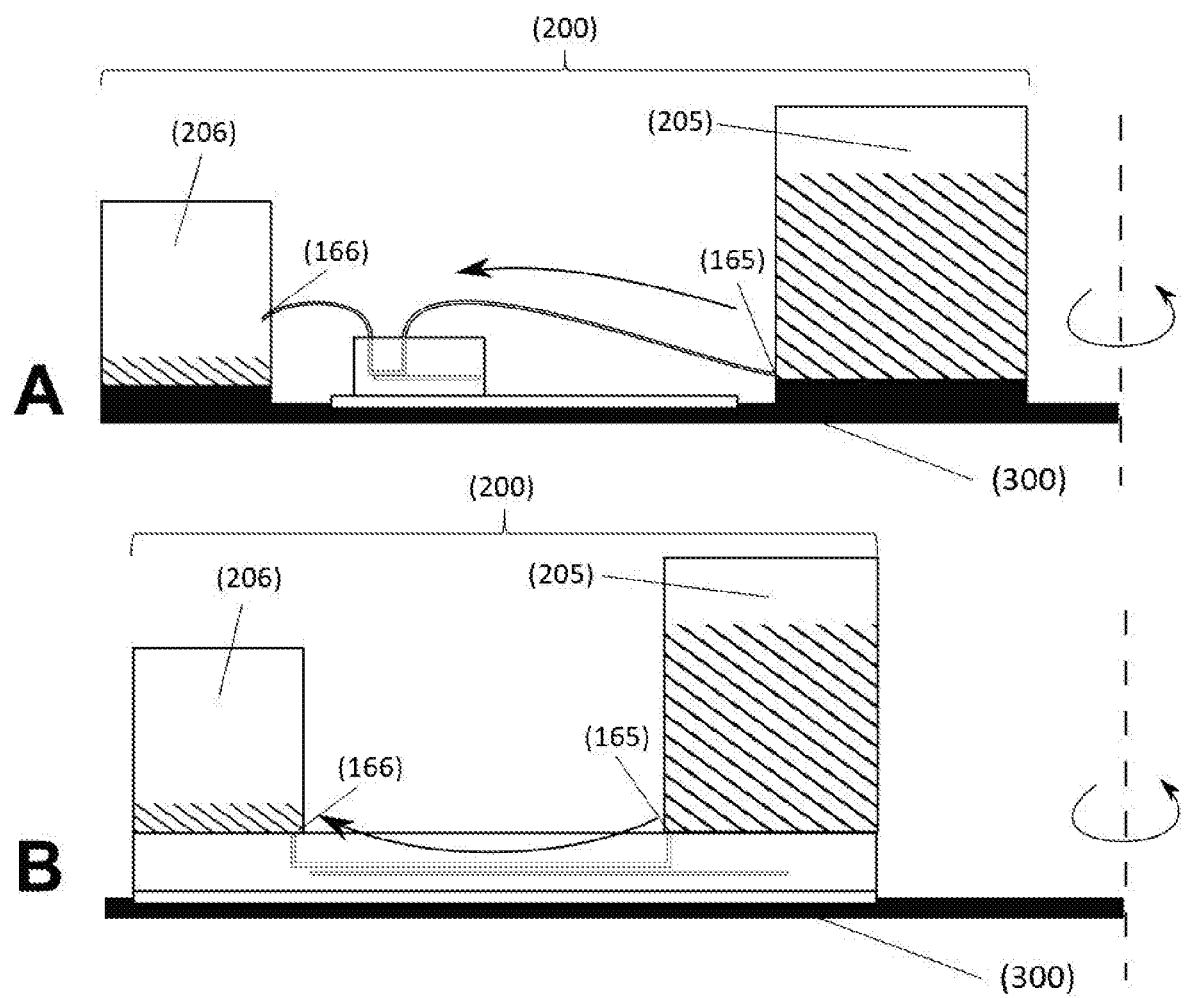
FIG. 30 shows the media supply of cultivation chambers via a separate (A) and integrated (B) reservoir.

FIG. 30 shows the media supply of cultivation chambers of a device used according to the invention on a rotational device (300) via a separate (A) and integrated (B) reservoir (200) having a separate container (205), which is arranged proximally to the axis of rotation of the rotation device (300), having a media outlet (165) and a separate container (206), which is arranged distally to the axis of rotation of the rotational device (300), having a media inlet (166).

FIG. 31 shows the volume flow determined experimentally by gravimetric measurement in a device according to the invention as a function of the speed of rotation (experimental) in comparison to the values determined by computer (theory).

The invention claimed is:

1. A method for producing a cell complex comprising
   a) providing cells and a device for cultivating cells, comprising a carrier plate unit comprising at least one first carrier plate and a second carrier plate arranged above or below the at least one first carrier plate, the at least one first carrier plate having at least one access opening, at least one cultivation chamber, and at least one channel connecting the at least one access opening to the at least one cultivation chamber, the second carrier plate having at least one media opening, at least one media chamber, and at least one media channel connecting the at least one media opening to the at least one media chamber,
   b) introducing the cells into the device through the at least one access opening,
   c) introducing the device into a rotational device enabling a rotation of the device for cultivating cells,
   d) setting the rotational device into rotation,
   e) receiving cells in the at least one cultivation chamber, and
   f) cultivating the cells in the at least one cultivation chamber,
   wherein a three-dimensional cell complex results due to the cultivation of the cells in the at least one cultivation chamber.

2. The method as claimed in claim 1, wherein the device for cultivating cells has a central axis of rotation and wherein the at least one access opening is arranged proximally to the axis of rotation and the cultivation chamber is arranged distally to the axis of rotation.

3. The method as claimed in claim 1, wherein the carrier plate unit has a central region having at least one connecting device comprising at least one through opening or at least one anchoring device, for the rotational device.

4. The method as claimed in claim 1, wherein the device for cultivating cells has at least one locking device for a rotational device.

5. The method as claimed in claim 4, wherein the at least one locking device is peripherally arranged.

6. The method as claimed in claim 1, wherein the at least one channel is a branched or unbranched channel.

7. The method as claimed in claim 1, wherein the at least one channel connects the at least one access opening to at least two cultivation chambers.

8. The method as claimed in claim 1, wherein the at least one channel has at least two cultivation chambers directly adjoining the at least one channel at least over a part of its length.

9. The method as claimed in claim 1, wherein the at least one channel is curved at least over a part of its length.

10. The method as claimed in claim 9 wherein the at least one channel has a static or angle-dependent curvature.

11. The method as claimed in claim 1, wherein the at least one access opening is designed as a loading chamber, which has at least two access openings.

12. The method as claimed in claim 1, wherein the at least one media channel connects at least two media openings to at least one media chamber.

13. The method as claimed in claim 1, wherein at least one separating device is arranged between the at least one first carrier plate and the second carrier plate.

14. The method as claimed in claim 13, wherein the at least one separating device comprises at least one membrane.

15. The method as claimed in claim 1, wherein the at least one cultivation chamber of the at least one first carrier plate and the at least one media chamber of the second carrier plate are formed overlapping and have a fluidic connection.

16. The method as claimed in claim 1, wherein the carrier plate unit additionally comprises a reservoir for liquids.

17. The method as claimed in claim 1, wherein the carrier plate unit has the form of a disk.

18. The method as claimed in claim 1, wherein the carrier plate unit is designed as a micro-titration plate.

19. The method as claimed in claim 1, wherein the carrier plate unit is constructed from glass or a polymer material.

20. The method as claimed in claim 1, wherein the carrier plate unit is constructed from polydimethyl siloxane (PDMS) or cycloolefin copolymers (COC).

21. The method as claimed in claim 1, further comprising the steps of:
   g) introducing cell culture medium into the at least one media opening,
   h) setting the rotational device into rotation, and
   i) receiving cell culture medium in the at least one media chamber to supply the cells in the cultivation chamber are carried out.

22. The method as claimed in claim 1, wherein a continuous or pulsed flow through the at least one media channel and at least one media chamber with cell culture medium is enabled by the generation of a pressure gradient, external or integrated pumps, or by rotation of the device for cultivating cells.

23. A cell culture comprising a cell composite produced according to a method as claimed in claim 1.

24. The method as claimed in claim 1, wherein the at least one media channel connects at least two media openings to at least two media chambers.

* * * * *

UNITED STATES PATENT AND TRADEMARK OFFICE
CERTIFICATE OF CORRECTION

PATENT NO. : 11,591,555 B2  
APPLICATION NO. : 16/621046  
DATED : February 28, 2023  
INVENTOR(S) : Peter Loskill et al.

Page 1 of 1

It is certified that error appears in the above-identified patent and that said Letters Patent is hereby corrected as shown below:

On the Title Page

Item [73], insert:  
--NMI Naturwissenschaftliches und Medizinisches Institut an der Universität Tübingen, Reutlingen (DE)--.

Signed and Sealed this  
First Day of August, 2023

Katherine Kelly Vidal  
*Director of the United States Patent and Trademark Office*